US006770659B2

(12) United States Patent
Choi et al.

(10) Patent No.: US 6,770,659 B2
(45) Date of Patent: Aug. 3, 2004

(54) BENZOYL PIPERIDINE COMPOUNDS

(75) Inventors: Yong-Moon Choi, Towaco, NJ (US); Yong-Kil Kim, Daejeon (KR); Jin-Uk Yoo, Daejeon (KR); Eun-Ah Paek, Daejeon (KR); Chun-Eung Park, Daejeon (KR); Sung-Yong Seo, Daejeon (KR); Coo-Min Chung, Daejeon (KR); Joon Heo, Daejeon (KR)

(73) Assignee: SK Corporation (KR)

( * ) Notice: Subject to any disclaimer, the term of this patent is extended or adjusted under 35 U.S.C. 154(b) by 0 days.

(21) Appl. No.: 10/228,869

(22) Filed: Aug. 26, 2002

(65) Prior Publication Data
US 2004/0044033 A1 Mar. 4, 2004

(51) Int. Cl.$^7$ ................. A61K 31/445; C07D 401/12
(52) U.S. Cl. ................. 514/326; 514/212; 514/235.5; 514/316; 514/330; 540/597; 544/130; 546/189; 546/210; 546/211; 546/225
(58) Field of Search .................. 514/212, 235.5, 514/316, 326, 330; 540/597; 544/130; 546/189, 210, 211, 225

(56) References Cited

U.S. PATENT DOCUMENTS

| | | | |
|---|---|---|---|
| 4,415,581 A | * 11/1983 | Davis et al. ................. 514/321 |
| 4,711,899 A | * 12/1987 | Gaudilliere et al. ........ 514/330 |
| 4,812,456 A | 3/1989 | Helsley et al. ............ 514/225.5 |
| 5,114,936 A | 5/1992 | Wettlaufer et al. ........ 514/233.8 |
| 5,935,974 A | * 8/1999 | Rae et al. .................... 514/326 |
| 6,365,604 B1 | * 4/2002 | Rae et al. .................... 514/326 |

FOREIGN PATENT DOCUMENTS

EP 409236 * 1/1991

OTHER PUBLICATIONS

Stedman's "medical dictionary" A Waverly co. pub. p.362 (1995).*

Bundgaard "Design of prodrugs" Elsevier p.7 (1986).*

* cited by examiner

Primary Examiner—Celia Chang
(74) Attorney, Agent, or Firm—Gibbons, Del Deo, Dolan, Griffinger and Vecchione

(57) ABSTRACT

Provided herein are racemic or enantiomerically enriched benzoyl piperidine compounds and pharmaceutically useful salts thereof, pharmaceutical compositions comprising an effective amount of racemic or enantiomerically enriched benzoyl piperidine compounds to treat central nervous system diseases and methods of treating central nervous system diseases in a mammal, in particular psychoses and cognition disorders.

39 Claims, No Drawings

BENZOYL PIPERIDINE COMPOUNDS

FIELD OF THE INVENTION

The present invention relates, in general, to racemic or enantiomerically enriched benzoyl piperidine compounds and pharmaceutically useful salts thereof, a pharmaceutical composition comprising an effective amount of racemic or enantiomerically enriched benzoyl piperidine compounds to treat central nervous system diseases and a method of treating central nervous system diseases in a mammal. More particularly, the present invention relates to racemic or enantiomerically enriched O-carbamoyl, alkoxy, azole or carbonate benzoyl piperidine compounds and pharmaceutically useful salts thereof, useful to treat the diseases of the central nervous system such as psychosis and cognition disorder. Also, the present invention is concerned with a process for preparing the same.

BACKGROUND OF THE INVENTION

Many reports have disclosed that benzoyl piperidine compounds are effectively used for controlling various central nervous system (CNS) disorders, especially as antipsychotic and analgesics.

1-[n-(2-alkylthio-10H-phenothiazin-10-yl)alkyl]-4-benzoylpiperidines were disclosed in U.S. Pat. No. 4,812,456 and 6,7-dihydro-3-phenyl-1,2-benzisoxazol-4(5H)-ones and -ols were disclosed in U.S. Pat. No. 5,114,936. These compounds are found to be very effective as therapeutical medicines for managing CNS disease, such as antipsychotic and analgesics.

Active research and development efforts have been continued to be directed to the application of benzoyl piperidine compounds for the treatment of CNS disorders.

SUMMARY OF THE INVENTION

A principal object of the present invention is to provide racemic or enantiomerically enriched benzoyl piperidine compounds, represented by the following structural formula (I) and pharmaceutically acceptable salts thereof:

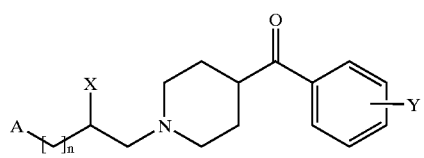

(I)

wherein n is 0; and

A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl and phenyl; thienyl; naphthyl; pyridyl; and quinolyl; or n is an integer from 1 to 2; and A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl and phenyl; thienyl; naphthyl; pyridyl; and quinolyl;

X is selected from the group consisting of O-carbamoyl, straight or branched chain alkoxy of from 1 to 4 carbon atoms, imidazole, triazole, tetrazole and carbonate; and Y is selected from the group consisting of hydrogen, halogen, straight or branched chain alkyl of from 1 to 4 carbon atoms and straight or branched chain alkoxy of from 1 to 3 carbon atoms.

More specifically, the present benzoyl piperidine compounds represented by the above formula (I) comprises racemic or enantiomerically enriched compounds represented by the following structural formula (V), (VIII), (XIV), and (XVI):

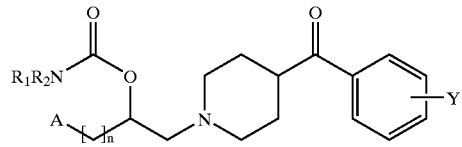

(V)

wherein n is 0; and

A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl; or n is an integer from 1 to 2; and A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl;

Y is selected from the group consisting of hydrogen, halogen, straight or branched chain alkyl of from 1 to 4 carbon atoms and straight or branched chain alkoxy of from 1 to 3 carbon atoms; and R1 and R2 may be the same with or different from each other and are independently selected from the group consisting of hydrogen, methoxy, benzyl and 5 to 7-membered aliphatic cyclic compounds:

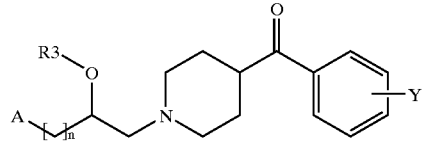

(VIII)

wherein n is 0; and

A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyl; thienyl; naphthyl; pyridyl; and quinolyl; or n is an integer from 1 to 2; and A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyl; thienyl; naphthyl; pyridyl; and quinolyl;

Y is selected from the group consisting of hydrogen, halogen, straight or branched chain alkyl of from 1 to 4 carbon atoms, and straight or branched chain alkoxy of from 1 to 3 carbon atoms; and R3 is selected from the group consisting of straight or branched chain alkyl of from 1 to 4 carbon atoms, aliphatic cyclic compound of from 5 to 7 carbon atoms, and benzyl:

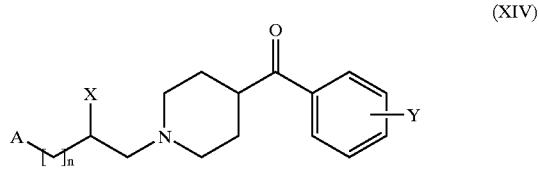

(XIV)

wherein n is an integer from 0 to 2;

A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl;

Y is selected from the group consisting of hydrogen, halogen, straight or branched chain alkyl of from 1 to 4 carbon atoms, and straight or branched chain alkoxy of from 1 to 3 carbon atoms; and X is imidazole, triazole, or tetrazole moiety having the following formula (XII):

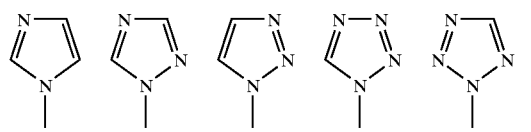

(XII)

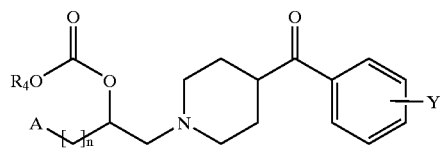

(XVI)

wherein n is 0 ; and

A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano and trifluoromethyl; or n is an integer from 1 to 2; and A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano and trifluoromethyl;

Y is selected from the group consisting of hydrogen, halogen, straight or branched chain alkyl of from 1 to 4 carbon atoms, and straight or branched chain alkoxy of from 1 to 3 carbon atoms; and R4 is selected from the group consisting of straight or branched chain alkyl of from 1 to 3 carbon atoms, phenyl and benzyl.

It is another object of the present invention to provide a pharmaceutical composition comprising an effective amount of racemic or enantiomerically enriched benzoyl piperidine compounds represented by the above structural formula (I), in particular, the compounds represented by the above structural formula (V), (VIII), (XIV) and (XVI), for treating disorders of central nervous system such as psychosis and cognition disorder.

It is still another object of the present invention to provide a method of treating disorders of central nervous system such as psychosis and cognition disorder in a mammal by administering an effective amount of racemic or enantiomerically enriched benzoyl piperidine compounds represented by the above structural formula (I), in particular, the compounds represented by the above structural formula (V), (VIII), (XIV) and (XVI) and a pharmaceutical acceptable carrier to a mammal in need of psychosis and cognition therapy.

DETAILED DESCRIPTION OF THE INVENTION

In accordance with the present invention, the compound represented by the structural formula I and pharmaceutical acceptable salts thereof can be prepared by the following steps starting from amino alcohol compounds represented by the following general structural formula (II):

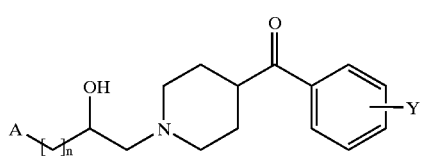

(II)

wherein n is 0; and

A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl and phenyl; thienyl; naphthyl; pyridyl; and quinolyl; or n is an integer from 1 to 2; and A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl and phenyl; thienyl; naphthyl; pyridyl; and quinolyl; and Y is selected from the group consisting of hydrogen, halogen, straight or branched chain alkyl of from 1 to 4 carbon atoms and straight or branched chain alkoxy of from 1 to 3 carbon atoms.

The method for preparing the amino alcohol compounds represented by the general structural formula (II) will be described below in detail.

Reacting epoxide represented by the following structural formula (III);

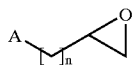
(III)

wherein n and A are the same as defined above;
with benzoyl piperidine represented by the following structural formula (IV):

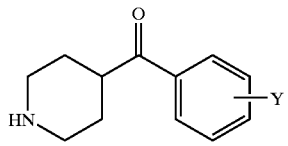
(IV)

wherein Y is the same as defined above;
to synthesize amino alcohol compounds represented by the structural formula (II).

It should be noted that the stereochemistry of the product (I, II, V, VIII, XIV and XVI) depends solely on that of the starting material (III); a starting material (III) with an (S)-enantiomer yields only a product with (S)-enantiomer and a starting material (III) with an (R)-enantiomer yields only a product with (R)-enantiomer.

The method for preparing the O-carbamoyl benzoyl piperidine compounds represented by the following general structural formula (V) will be described below in detail.

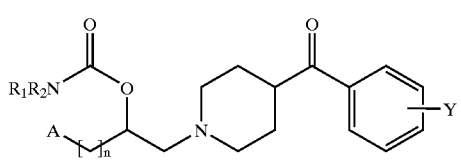
(V)

wherein
n is 0; and
A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl; or n is an integer from 1 to 2; and A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl;

Y is selected from the group consisting of hydrogen, halogen, straight or branched chain alkyl of from 1 to 4 carbon atoms and straight or branched chain alkoxy of from 1 to 3 carbon atoms; and R1 and R2 may be the same with or different from each other and are independently selected from the group consisting of hydrogen, methoxy, benzyl and 5 to 7-membered aliphatic cyclic compounds.

The O-carbamoyl benzoyl piperidine compounds represented by the general structural formula (V) are prepared by reacting amino alcohol represented by the general structural formula (II) with 1,1'-carbonyldiimidazole and then with amine base represented by the following general structural formula (VI);

R1R2NH (VI)

wherein R1 and R2 are the same as defined above.

This procedure is summarized as set forth in Reaction Scheme I below.

Reaction Scheme I

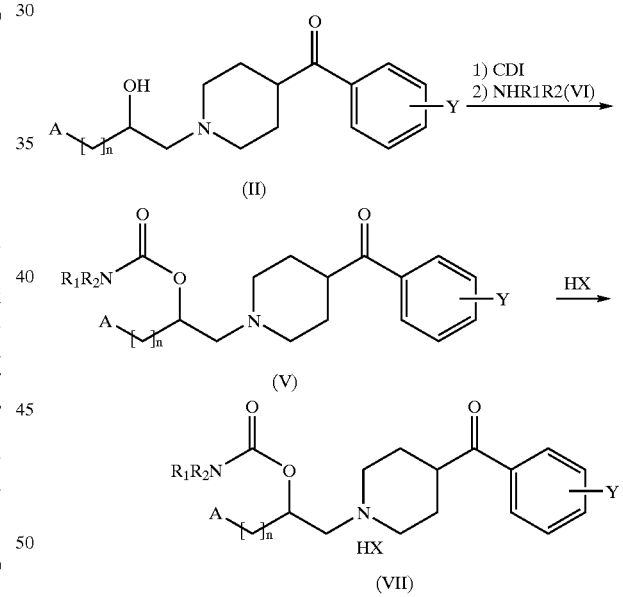

Details of the reaction conditions described in Reaction Scheme I are as follows. For the conversion of the compounds (II) to the compound (V), the concentration of the starting material (II) is about 0.005 to 0.1 moles with 1,1'-carbonyldiimidazole ranging from about 2.0 to 3.0 equivalents. This reaction is preferably carried out at a temperature of 10 to 30° C. Without purification, the resulting intermediate is treated with 1 to 1,000 equivalents of amine base represented by the general formula (VI) at a temperature of 10 to 30° C. to give the compound of the general formula (V). For this carbamoylation, an ethereal solvent such as diethyl ether and tetrahydrofuran, a halogenated hydrocarbon solvent such as dichloromethane and chloroform, or the mixture thereof may be used.

In Reaction Scheme I, HX represents an acid capable of forming a pharmacologically useful salt with the basic nitrogen atom. Specific examples of the anhydrous acid used for the preparation of the compound (VII) from the compound (V) include hydrochloric acid, sulfuric acid, phosphoric acid, acetic acid, benzoic acid, citric acid, malonic acid, salicylic acid, malic acid, fumaric acid, oxalic acid, succinic acid, tartaric acid, lactic acid, gluconic acid, ascorbic acid, maleic acid, aspartic acid, benzene sulfonic acid, methane sulfonic acid, ethane sulfonic acid, hydroxymethane sulfonic acid and hydroxyethane sulfonic acid and the like. Additional acids can refer to "Pharmaceutical Salts", *J. Pharm. Sci.,* 1977; 66(1): 1–19. This preparation is executed in a reaction media which can be exemplified by an ethereal solvent such as tetrahydrofuran, an alcoholic solvent such as.methanol, an ester solvent such as ethyl acetate, a halogenated hydrocarbon solvent, and the mixtures thereof. An ethereal solvent is recommended as an addition solution, including ethyl ether, propyl ether, isopropyl ether, butyl ether, isobutyl ether. The concentration of the compound (V) is on the order of about 0.01 to 5 moles.

The method for preparing the alkoxy benzoyl piperidine compounds represented by the following general structural formula (VIII) will be described below in detail.

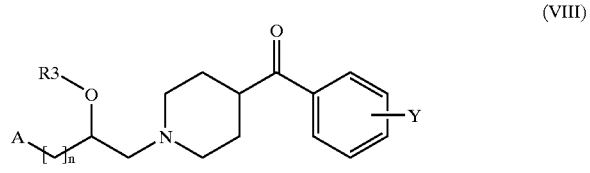

(VIII)

wherein n is 0; and

A is selected from the group consisting of phenyl which may be substituted with one or more identical or different substituents selected from the group consisting of hydrogen, halogen, straight or branched chain alkyl of from. 1 to 4 carbon atoms, straight or branched chain alkoxy of from 1 to 3 carbon atoms, nitro, cyano, trifluoromethyl, trifluoromethoxy, methanesulfonyl, phenyl; thienyl; naphthyl; pyridyl; and quinolyl; or n is an integer from 1 to 2; and A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyl; thienyl; naphthyl; pyridyl; and quinolyl;

Y is selected from the group consisting of hydrogen, halogen, straight or branched chain alkyl of from 1 to 4 carbon atoms, and straight or branched chain alkoxy of from 1 to 3 carbon atoms; and R3 is selected from the group consisting of straight or branched chain alkyl of from 1 to 4 carbon atoms, aliphatic cyclic compound of from 5 to 7 carbon atoms, and benzyl.

The alkoxy benzoyl piperidine compounds represented by the general structural formula (VIII) is prepared by reacting amino alcohol represented by the general structural formula (II) with methanesulfonyl chloride and triethylamine and then with alcohol represented by the following general structural formula (IX);

R3OH (IX)

wherein R3 is the same as defined above.

The alternative method for conversion of amino alcohol compounds (II) to alkoxy benzoyl piperidine compounds of the general structural formula (VIII) in which A is phenoxy is to react amino alcohol represented by the general structural formula (II) with sodium hydride and then with alkyl halide represented by the following general structural formula (X) to produce alkoxy benzoyl piperidine compounds represented by the general structural formula (VIII);

R3Z (X)

wherein Z is a halogen atom such as chloride, bromide or iodide.

The pharmaceutically acceptable salts thereof can be obtained by treating alkoxy benzoyl piperidine compounds (VIII) with an anhydrous acid in a solution without further purification.

This procedure is summarized as set forth in Reaction Scheme II below.

Reaction Scheme II

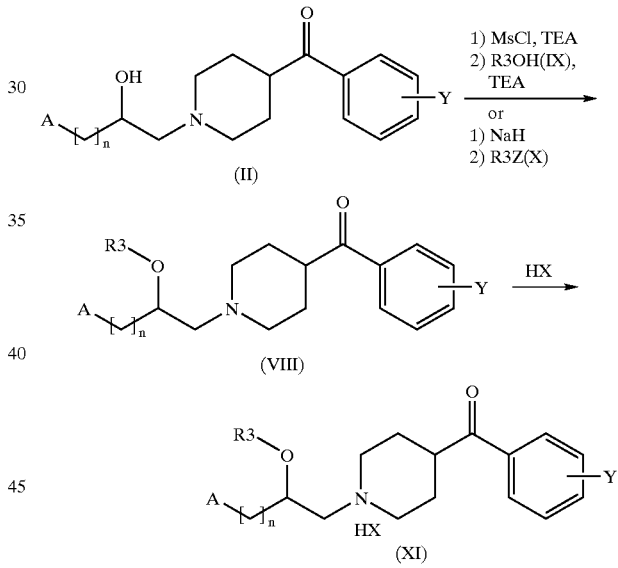

Details of the reaction conditions described in Reaction Scheme II are as follows. For the conversion of the compounds (II) to the compound (VIII), the concentration of the starting material (II) is about 0.005 to 0.1 moles with methanesulfonyl chloride ranging from about 3.0 to 4.0 equivalents and triethylamine ranging from about 3.0 to 4.0 equivalents. This reaction is preferably carried out at a temperature of 0 to 30° C. Without purification, the resulting intermediate is treated with 1 to 1,000 equivalents of alcohol represented by the general formula (IX) at a temperature of 30 to 90° C. to give the compound of the general formula (VIII). For this alkylation, an ethereal solvent such as diethyl ether and tetrahydrofuran, a halogenated hydrocarbon solvent such as dichloromethane and chloroform, an alcohol solvent such as methanol, ethanol and propanol, or the mixture thereof may be used.

For the alternative conversion of compound (II) to the compound (VIII) in which A is phenoxy, the concentration of the starting material (II) is about 0.01 to 0.1 moles with sodium hydride ranging from about 1.0 to 2.0 equivalents. The mixture is treated with 1.0 to 2.0 equivalents of alkyl halide represented by the general formula (X). This reaction is preferably carried out at a temperature of 0 to 20° C. For this alkylation, an ethereal solvent such as diethyl ether and tetrahydrofuran, a halogenated hydrocarbon solvent such as dichloromethane and chloroform, or the mixture thereof may be used.

In Reaction Scheme II, HX represents an acid capable of forming a pharmacologically useful salt with the basic nitrogen atom.

The method for preparing the azole benzoyl piperidine compounds represented by the general structural formula (XIV) in which X is imidazole, triazole or tetrazole moiety having the following general structural formula (XII) will be described below in detail.

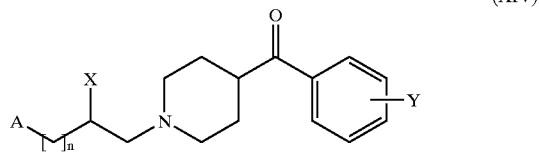

(XIV)

wherein
n is an integer from 0 to 2;
A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl;
Y is selected from the group consisting of hydrogen, halogen, straight or branched chain alkyl of from 1 to 4 carbon atoms, and straight or branched chain alkoxy of from 1 to 3 carbon atoms; and
X is imidazole, triazole, or tetrazole moiety having the following formula (XII):

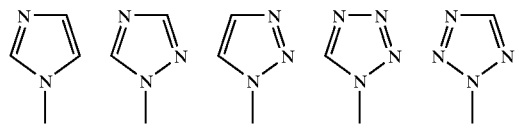

(XII)

The azole benzoyl piperidine compounds represented by the general structural formula (XIV) in which X is imidazole, triazole or tetrazole moiety having the general structural formula (XII) is prepared by reacting amino alcohol represented by the general structural formula (II) with methanesulfonyl chloride and triethylamine and then with azole represented by the following general structural formula (XIII):

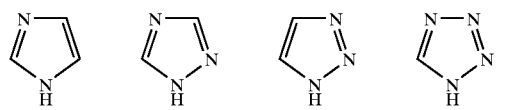

(XIII)

The pharmaceutically acceptable salts thereof can be obtained by treating azole benzoyl piperidine compounds with an anhydrous acid in a solution without further purification.

This procedure is summarized as set forth in Reaction Scheme III below.

Reaction Scheme III

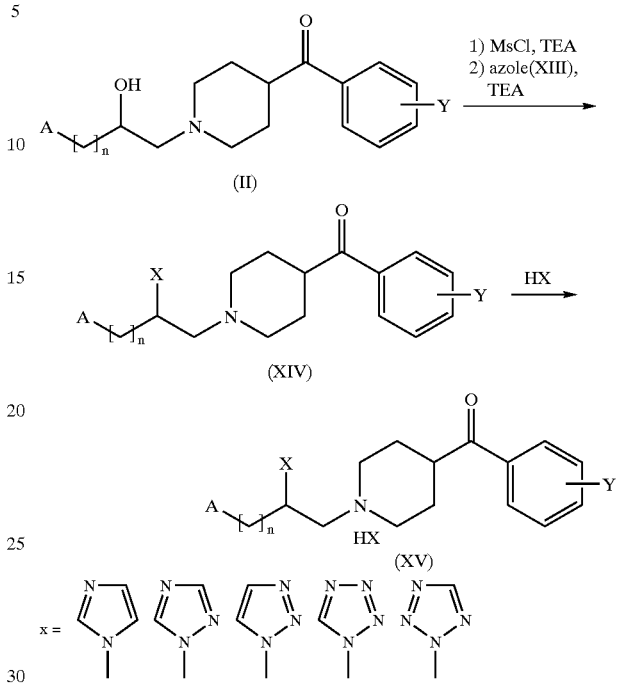

Details of the reaction conditions described in Reaction Scheme III are as follows. For the conversion of the compounds (II) to the compound (XIV) in which X is imidazole, triazole or tetrazole moiety having the general structural formula (XII), the concentration of the starting material (II) is about 0.005 to 0.1 moles with methanesulfonyl chloride ranging from about 1.0 to 3.0 equivalents and triethylamine ranging from about 1.0 to 3.0 equivalents. This reaction is preferably carried out at a temperature of 0 to 30° C. Without purification, the resulting intermediate is treated with 3 to 4 equivalents of azole represented by the general formula (XIII) at a temperature of 30 to 90° C. to give the compound of the general formula (XV). For this reaction, an ethereal solvent such as diethyl ether and tetrahydrofuran, a halogenated hydrocarbon solvent such as dichloromethane and chloroform, or the mixture thereof may be used.

In Reaction Scheme III, HX represents an acid capable of forming a pharmacologically useful salt with the basic nitrogen atom.

The method for preparing the carbonate benzoyl piperidine compounds represented by the following general structural formula (XVI) will be described below in detail.

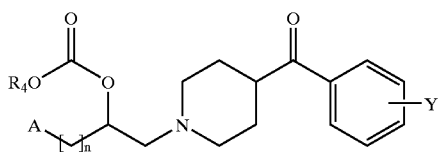

(XVI)

wherein
n is 0; and
A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano and trifluoromethyl; or n is an integer from 1 to 2; and A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano and trifluoromethyl;

Y is selected from the group consisting of hydrogen, halogen, straight or branched chain alkyl of from 1 to 4 carbon atoms, and straight or branched chain alkoxy of from 1 to 3 carbon atoms; and R4 is selected from the group consisting of straight or branched chain alkyl of from 1 to 3 carbon atoms, phenyl and benzyl.

The carbonate benzoyl piperidine compounds represented by the general structural formula (XVI) is prepared by reacting amino alcohol represented by the general structural formula (II) with 1,1'-carbonyldiimidazole and then with alcohol represented by the following general structural formula (XVII):

R4OH (XVII)

wherein R4 is the same as defined above.

The pharmaceutically acceptable salts thereof can be obtained by treating carbonate benzoyl piperidine compounds with an anhydrous acid in a solution without further purification.

This procedure is summarized as set forth in Reaction Scheme IV below.

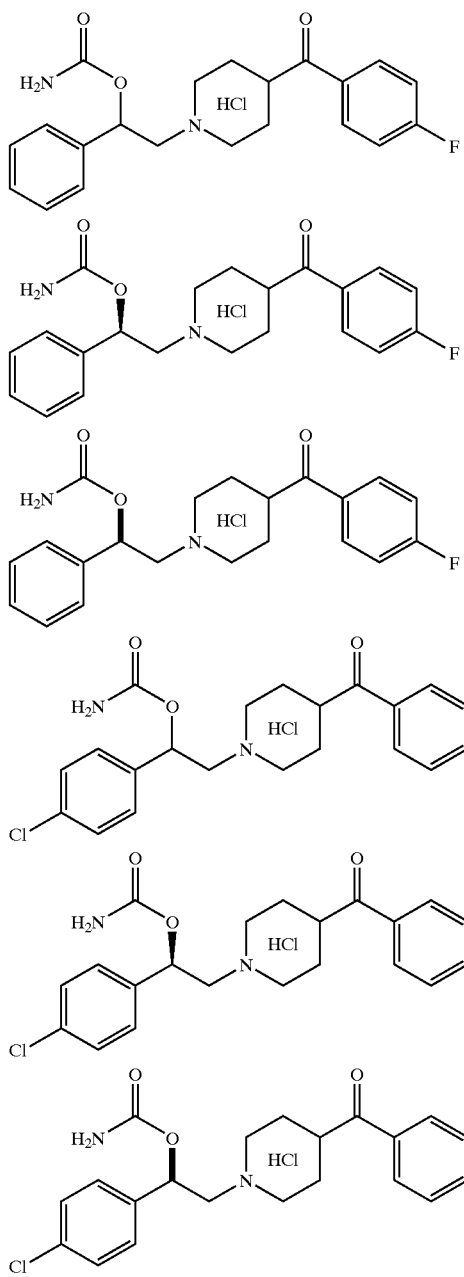

Details of the reaction conditions described in Reaction Scheme IV are as follows. For the conversion of the compounds (II) to the compound (XVI), the concentration of the starting material (II) is about 0.005 to 0.1 moles with 1,1'-carbonyldiimidazole ranging from about 2.0 to 3.0 equivalents. This reaction is preferably carried out at a temperature of 10 to 30° C. Without purification, the resulting intermediate is treated with 1 to 1,000 equivalents of alcohol represented by the general formula (XVII) at a temperature of 10 to 30° C. to give the compound of the general formula (XVI). For this carbonylation, an ethereal solvent such as diethyl ether and tetrahydrofuran, a halogenated hydrocarbon solvent such as dichloromethane and chloroform, or the mixture thereof may be used.

In Reaction Scheme IV, HX represents an acid capable of forming a pharmacologically useful salt with the basic nitrogen atom.

Representative examples of the compounds (I), (V), (VIII), (XIV) and (XVI) from scheme I, II, III and IV include the following structures:

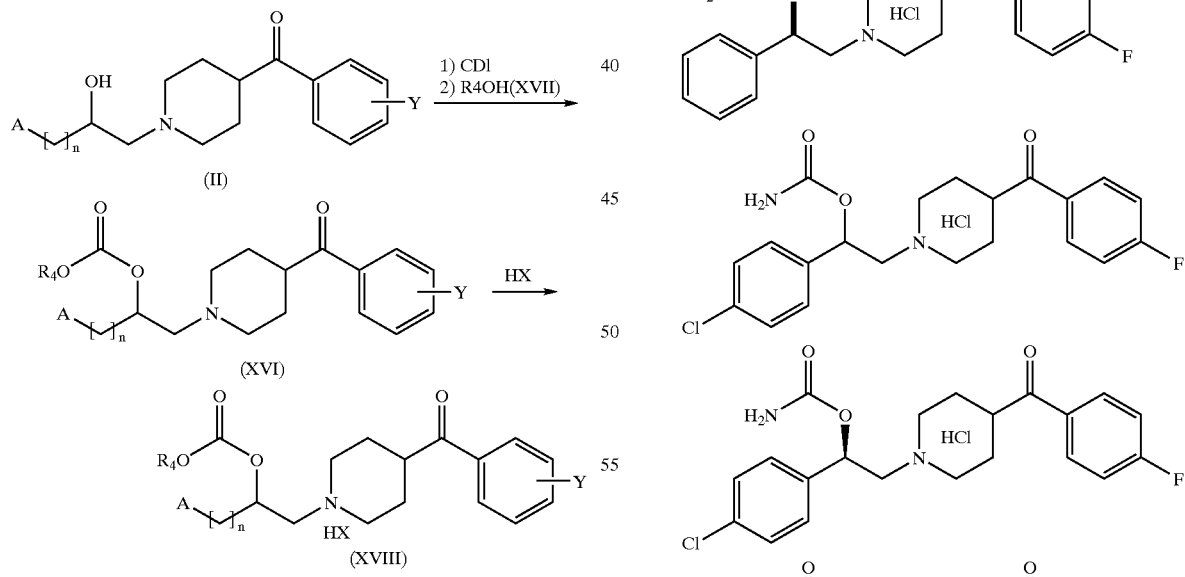

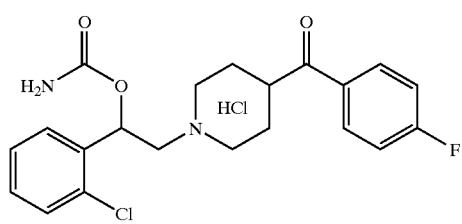
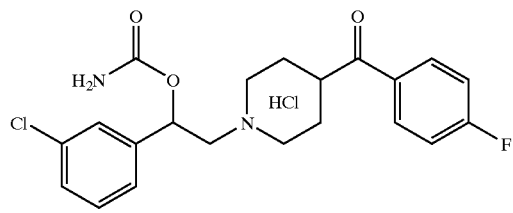
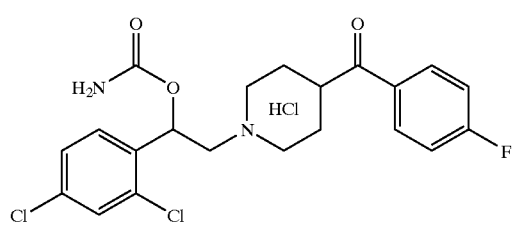
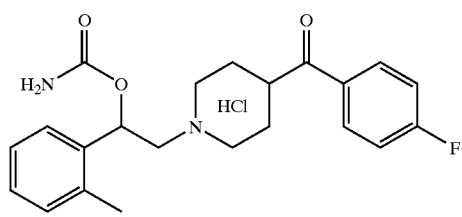
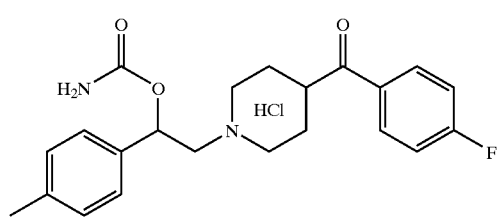
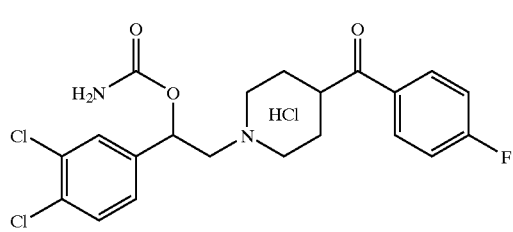
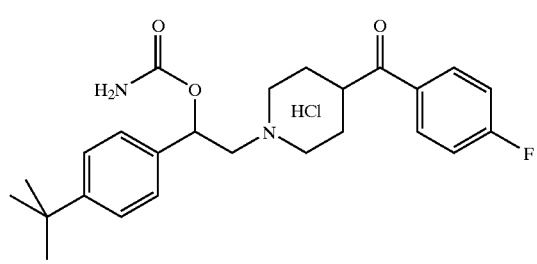
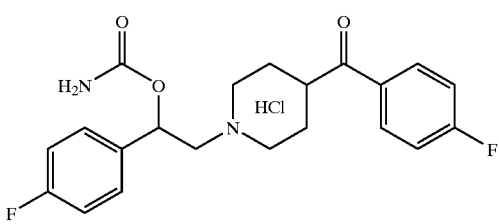
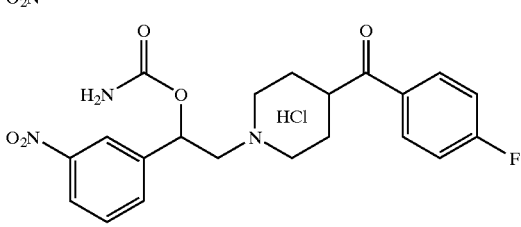
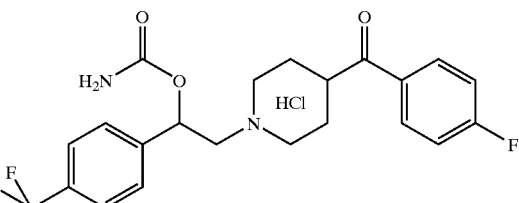
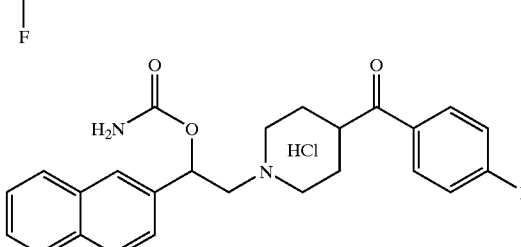
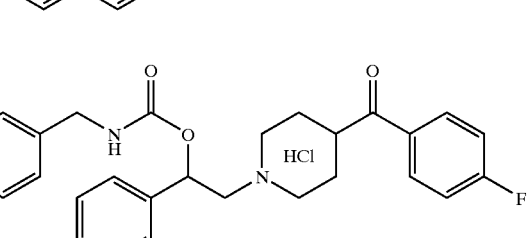
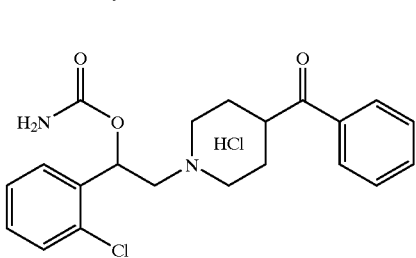

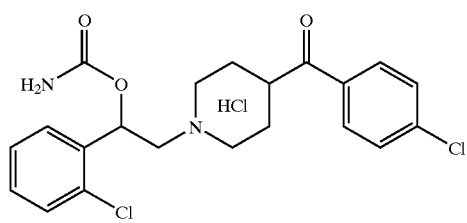
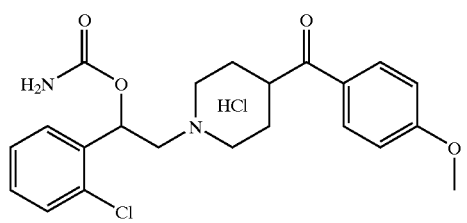
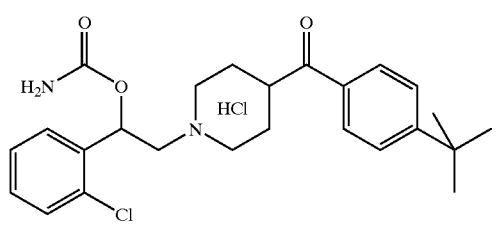
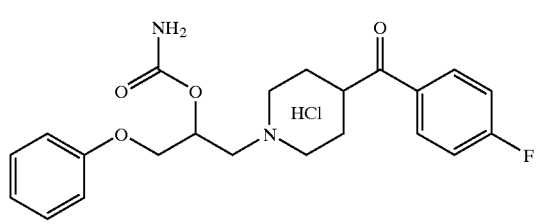
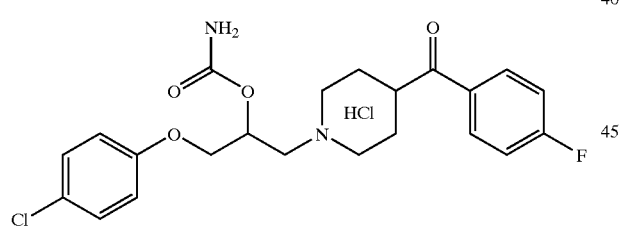
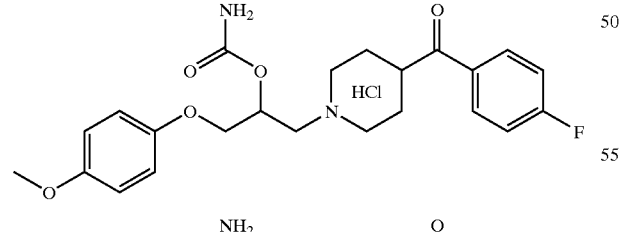
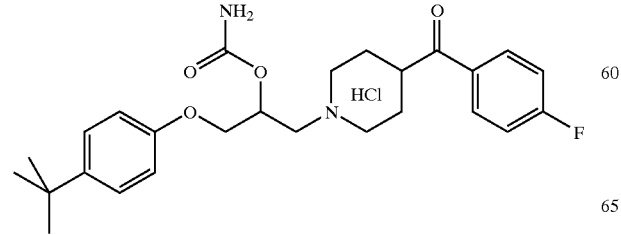
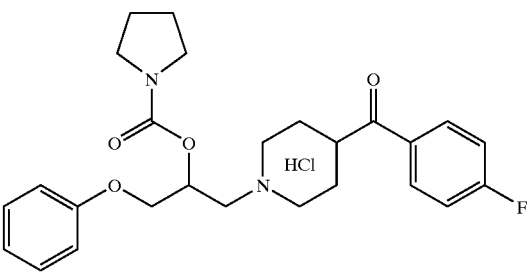
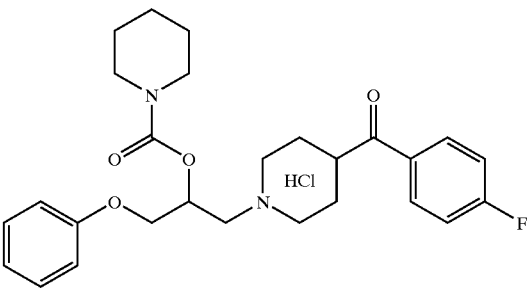
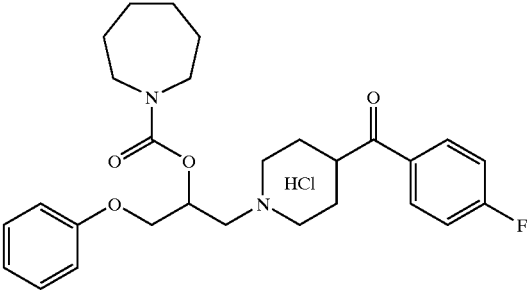
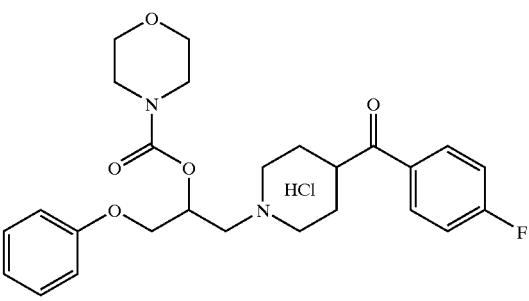
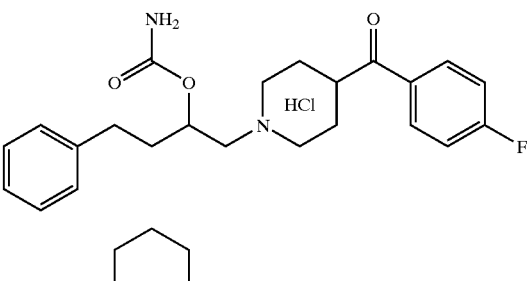
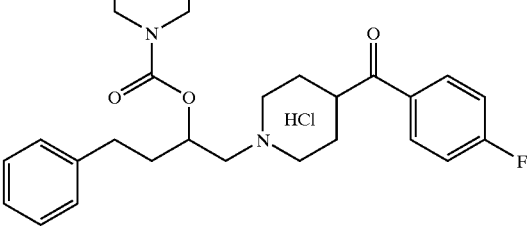

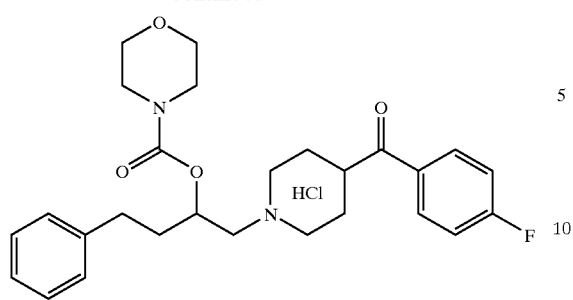
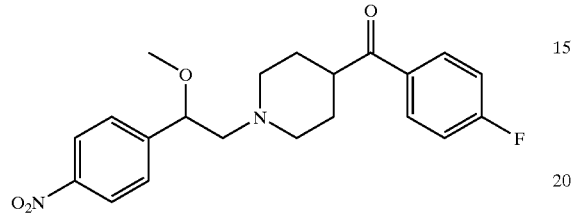
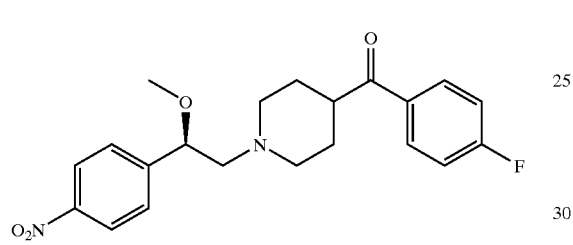
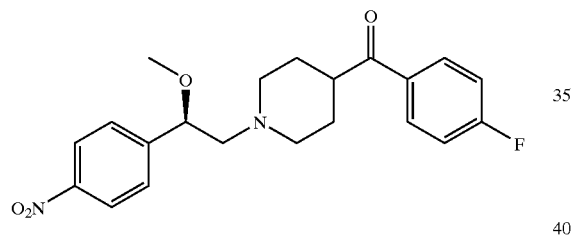
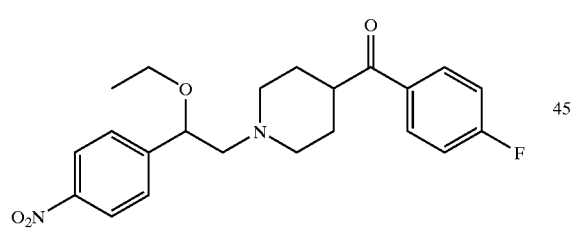
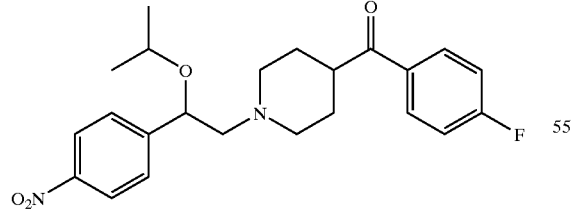
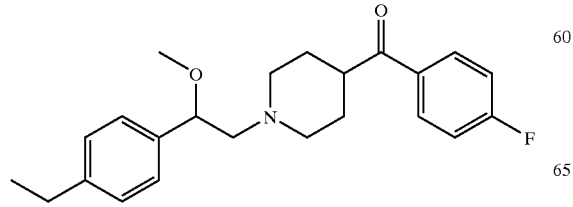
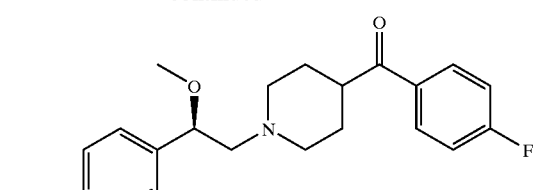
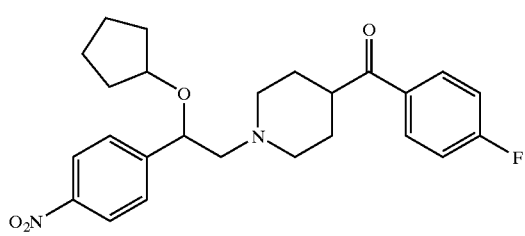
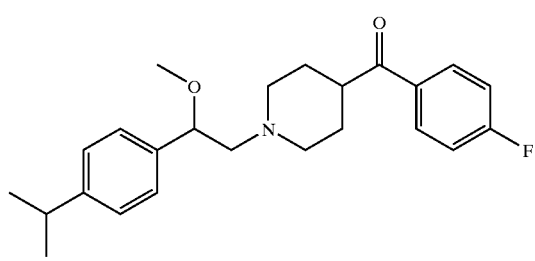
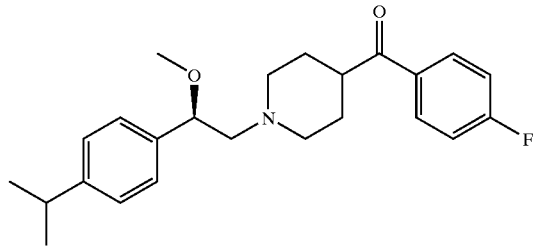
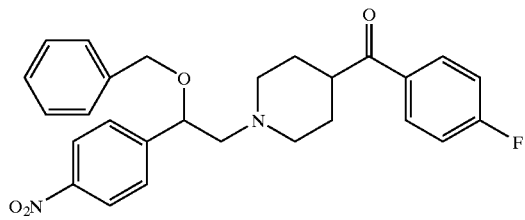
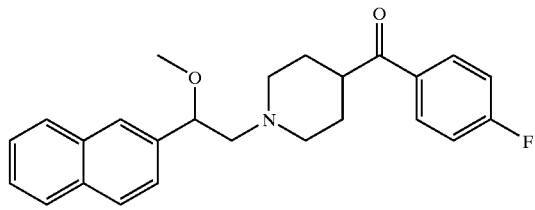
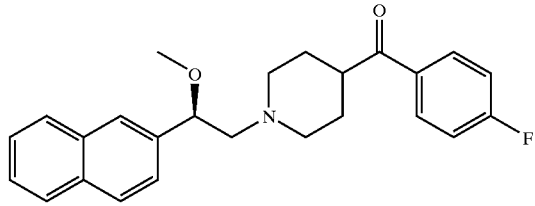

-continued
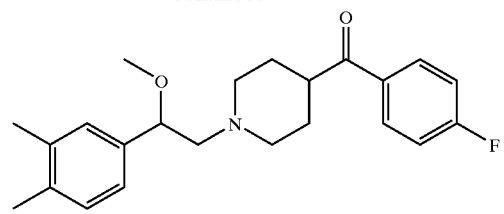
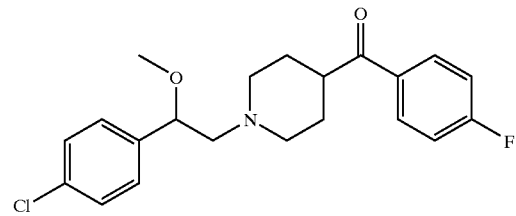
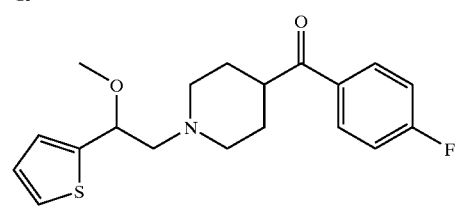
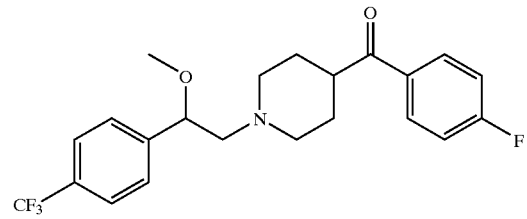
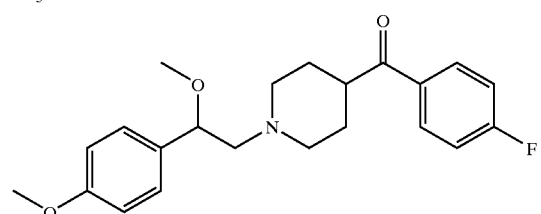
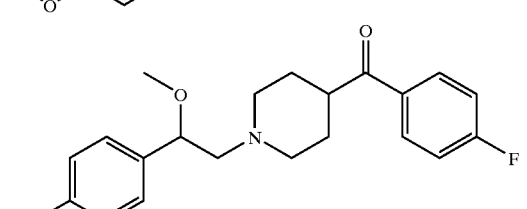
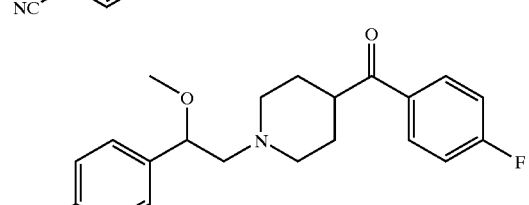
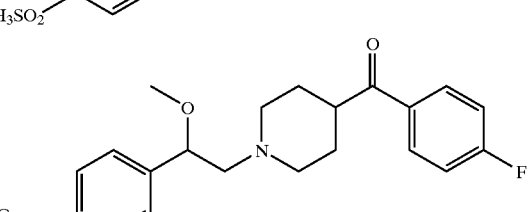
-continued
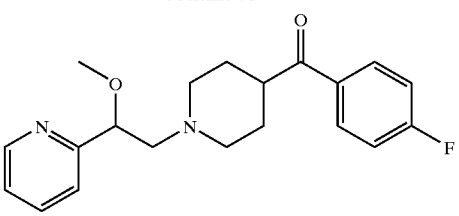
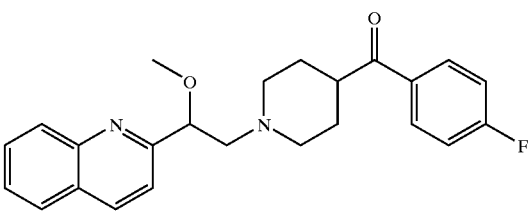
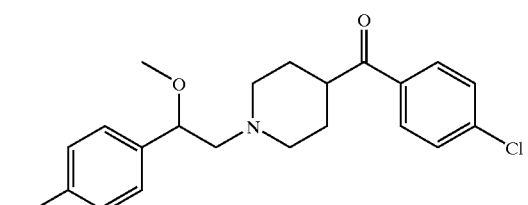
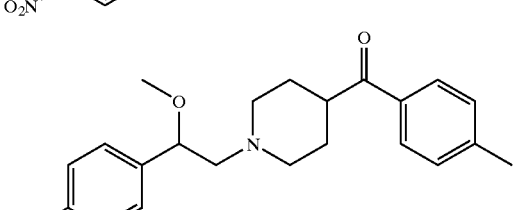
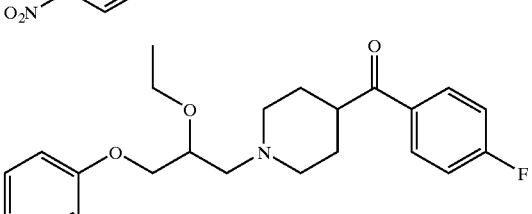
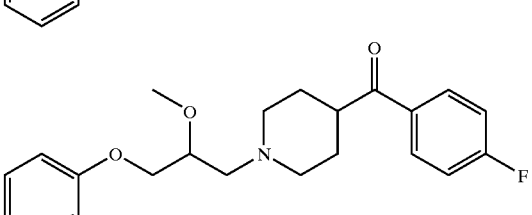
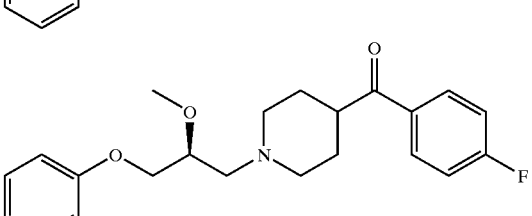
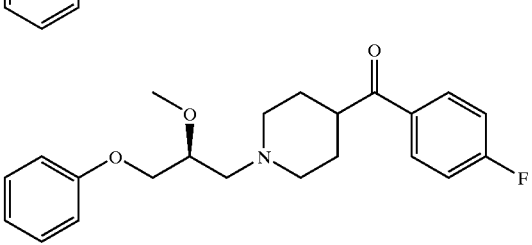

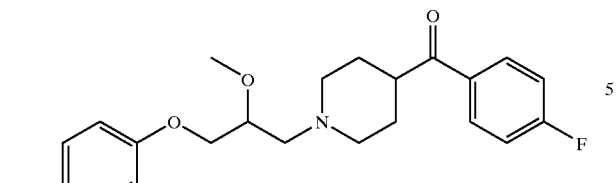
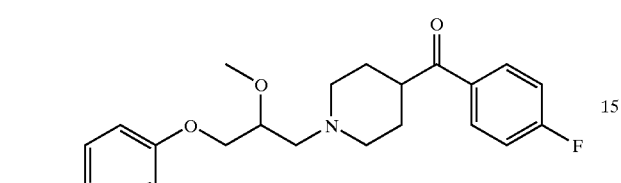
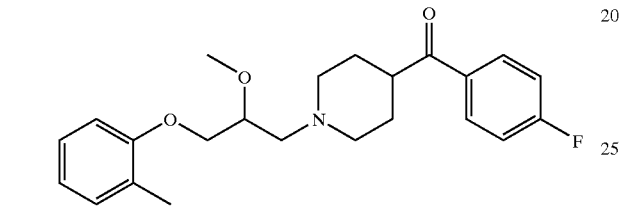
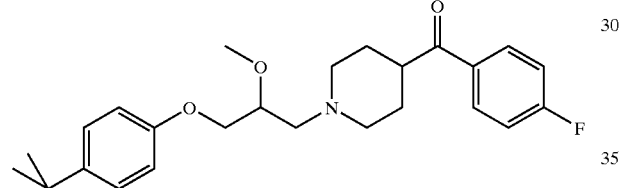
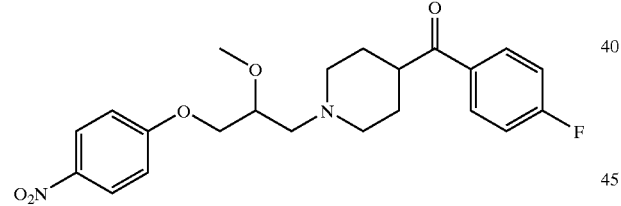
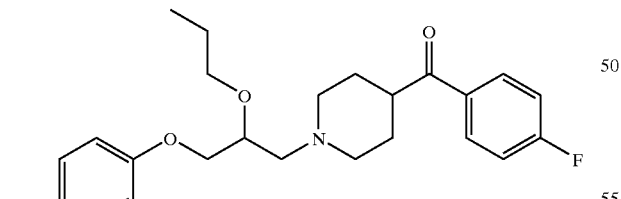
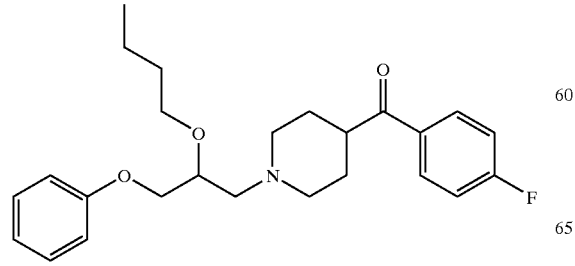
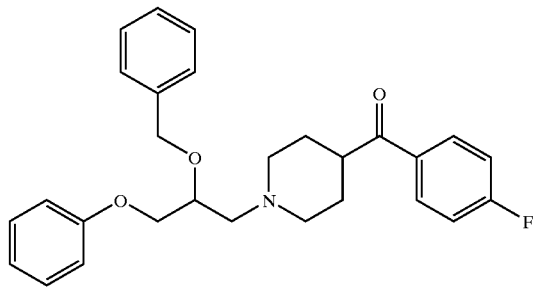
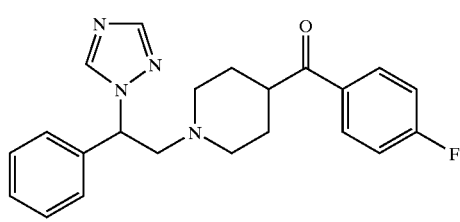
3HCl
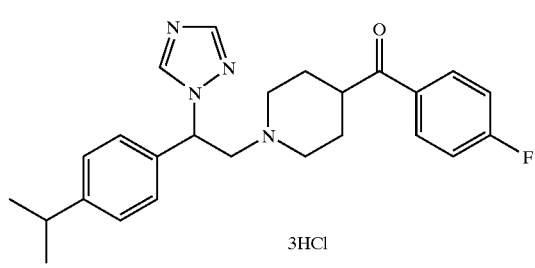
3HCl
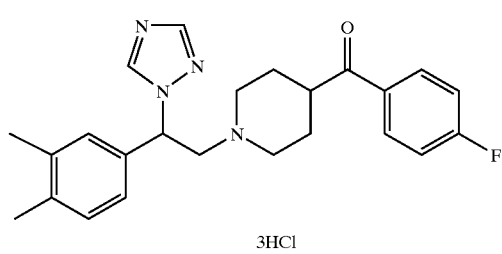
3HCl
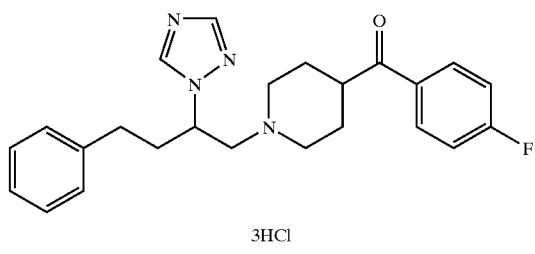
3HCl
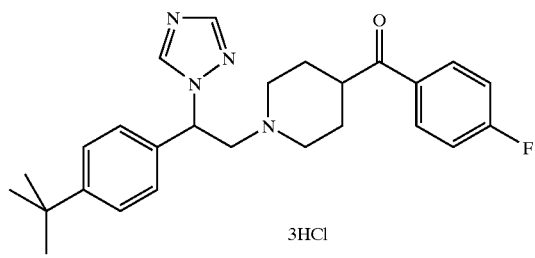
3HCl -continued

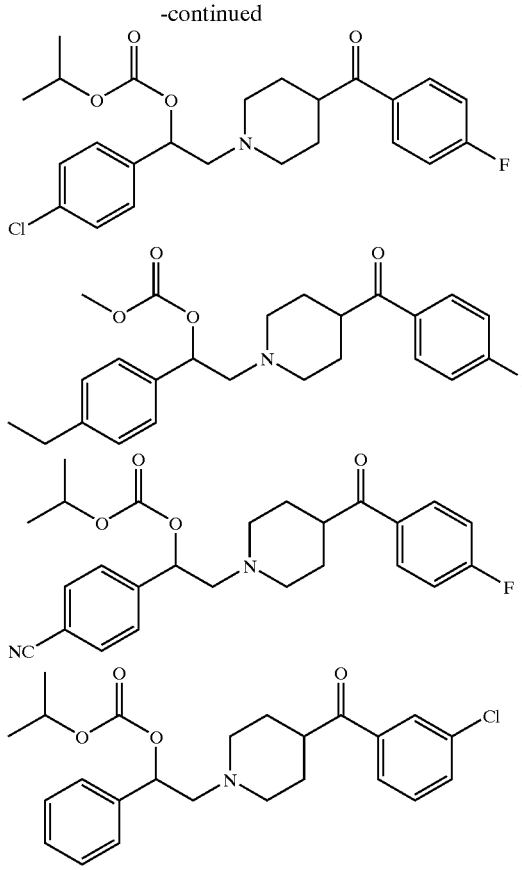

The present invention includes methods of treating psychosis and cognition disorders in a mammal which comprises administering the composition of the compound of structural formula (I), (V), (VIII), (XIV) and (XVI) to a mammal in need of psychosis and cognition therapy.

This activity was examined through the anti-climbing behavior test, i.e. the test for suppressing the climbing behavior induced by apomorphine in mice. A designated amount of the test compound was intraperitoneally or orally administered to several groups of ICR CD strain male mice (body weight, 20 to 25 g; one group, 6 mice), and each of the animals was charged in an individual column cage of 12 cm in diameter and 14 cm in height having metal poles (each pole, 2 mm in diameter) vertically installed and arranged along the periphery with interval of 1 cm.

Compounds to be tested for antipsychotic activity are injected intraperitoneally or given orally at various time intervals, e.g. 30 minutes, 60 minutes, etc., prior to the apomorphine challenge at a screening dose of 0.1–60 mg/kg.

For evaluation of climbing, 3 readings are taken at 10, 20 and 30 minutes after apomorphine administration according to the following scale:

| Score | Evaluation |
|---|---|
| 0 | All the paws were on the floor |
| 1 | One paw seized the pole of the cage |
| 2 | Two paws seized the pole of the cage |
| 3 | Three paws seized the pole of the cage |
| 4 | All four paws seized the pole of the cage |

Mice consistently climbing before the injection of apomorphine will be discarded.

With full-developed apomorphine climbing, the animals are hanging on to the cage walls, rather motionless, over longer periods of time. By contrast, climbing due to mere motor stimulation usually only lasts a few seconds.

The climbing scores are individually totaled (maximal score: 12 per mouse over 3 readings) and the total score of the control group (vehicle intraperitoneally-apomorphine subcutaneously) is set to 100%. ED50 values with 95% confidence limits, calculated by a linear regression analysis, of some of the compounds of the instant invention as well as a standard antipsychotic agent are presented in Table I.

TABLE 1

Climbing Mouse Assay

| COMPOUND | $ED_{50}$ mg/kg i.p. | p.o. |
|---|---|---|
| carbamic acid 2-[4-(4-fluoro-benzoyl)-piperidin-1-yl]-1-phenyl-ethyl ester | 4.8 | 9.7 |
| (S)-carbamic acid 2-[4-(4-fluoro-benzoyl)-piperidin-1-yl]-1-phenyl-ethyl ester | 0.96 | 4.3 |
| (R)-carbamic acid 2-[4-(4-fluoro-benzoyl)-piperidin-1-yl]-1-phenyl-ethyl ester | 17.8 | 46.2 |
| carbamic acid 1-(3-chloro-phenyl)-2-[4-(4-fluoro-benzoyl)-piperidin-1-yl]-ethyl ester | 0.56 | 0.94 |
| carbamic acid 1-(3,4-dichloro-phenyl)-2-[4-(4-fluoro-benzoyl)-piperidin-1-yl]-ethyl ester | 0.32 | 0.48 |
| benzyl-carbamic acid 2-[4-(4-fluoro-benzoyl)-piperidin-1-yl]-phenyl-ethyl ester | 2.2 | 7.1 |
| carbamic acid 2-[4-(4-fluoro-benzoyl)-piperidin-1-yl]-1-(3-nitro-phenyl)-ethyl ester | 2.6 | — |
| carbamic acid 2-[4-(4-fluoro-benzoyl)-piperidin-1-yl]-1-(4-trifluoromethyl-phenyl)-ethyl ester | 1.8 | — |
| carbamic acid 1-[4-(4-fluoro-benzoyl)-piperidin-1-ylmethyl]-2-phenoxy-ethyl ester | 2.0 | 8.5 |
| carbamic acid Azepane-1-carboxylic acid 1-[4-(4-fluoro-benzoyl)-piperidin-1-ylmethyl]-2-phenoxy-ethyl ester | 1.5 | — |
| (4-fluoro-phenyl)-{1-[2-methoxy-2-(4-nitro-phenyl)-ethyl]-piperidin-4-yl}-methanone | 5.9 | 51.2 |
| (S)-(4-fluoro-phenyl)-{1-[2-methoxy-2-(4-nitro-phenyl)-ethyl]-piperidin-4-yl}-methanone | 4.5 | 16.9 |
| (R)-(4-fluoro-phenyl)-{1-[2-methoxy-2-(4-nitro-phenyl)-ethyl]-piperidin-4-yl}-methanone | 24.2 | — |
| (4-fluoro-phenyl)-{1-[2-(4-isopropyl-phenyl)-2-methoxy-ethyl]-piperidin-4-yl}-methanone | 0.17 | 0.41 |
| (S)-(4-fluoro-phenyl)-{1-[2-(4-isopropyl-phenyl)-2-methoxy-ethyl]-piperidin-4-yl}-methanone | 0.13 | 0.09 |
| {1-[2-(4-ethyl-phenyl)-2-methoxy-ethyl]-piperidin-4-yl}-(4-fluoro-phenyl)-methanone | 0.87 | |
| (S)-{1-[2-(4-ethyl-phenyl)-2-methoxy-ethyl]-piperidin-4-yl}-(4-fluoro-phenyl)-methanone | 0.31 | 1.2 |
| {1-[2-ethoxy-2-(4-nitro-phenyl)-ethyl]-piperidin-4-yl}-(4-fluoro-phenyl)-methanone | 4.16 | — |
| (4-fluoro-phenyl)-{1-[2-(4-isopropyl-phenyl)-2-[1,2,4]triazol-1-yl-ethyl]-piperidin-4-yl}-methanone | 3.1 | 4.7 |
| {1-[2-(3,4-dimethyl-phenyl)-2-[1,2,4]triazol-1-yl-ethyl]-piperidin-4-yl}-(4-fluoro-phenyl)-methanone | 4.5 | 16.6 |
| carbonic acid 1-(4-ethyl-phenyl)-2-[4-(4-fluoro-benzoyl)-piperidin-1-yl]-ethyl ester methyl ester | 2.4 | 7.6 |
| carbonic acid 1-(3-chloro-phenyl)-2-[4-(4-fluoro-benzoyl)-piperidin-1-yl]-isopropyl ester isopropyl ester | 6.2 | — |
| Risperidone (standard) | 0.11 | 0.29 |
| Clozapine (standard) | 6.3 | 13.5 |

In therapeutic use as agents for various CNS disorders such as psychosis and cognition disorder, the compounds of the present invention, alone or in combination with pharmaceutically acceptable carrier, are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of patient's condition and the activity of the compound. The determination of optimum dosages for a particular situation must clinically be done and is within the skill of the art.

In utilizing the compounds of the present -invention for the central nervous system, it is preferred to administer the compounds orally. Since the compounds absorb well orally, it usually will riot be necessary to resort to parenteral administration. For oral administration, the compounds having the general formula I is preferably combined with a pharmaceutical carrier. The ratio of the carrier to the compound of structural formula I is not critical to express the effects of the medicine on the central nervous system, and they can vary considerably depending on whether the composition is to be filled into capsules or formed into tablets. In tableting, various edible pharmaceutical carriers or the mixture thereof can be used. Suitable carriers, for example, are a mixture of lactose, diabasic calcium phosphate and/or corn starch. Other pharmaceutically acceptable ingredients can be further added, including lubricants such as magnesium stearate.

A better understanding of the present invention may be obtained in light of following examples which are set forth to illustrate, but are not to be construed to limit, the present invention.

EXAMPLE 1

Carbamic acid 2-[4-(4-fluoro-benzoyl)-piperidin-1-yl]-1-phenyl-ethyl ester; hydrochloride A mixture of 4-(4-fluorobenzoyl)piperidine (5 mmol) and styrene oxide(5 mmol) was refluxed in 30 ml of isopropanol for 4 h. This solution was then concentrated on a rotary evaporator and diluted with ethyl acetate. This mixture was then washed with brine, the resulting organic layer was dried and concentrated in vacuo. The crude product was dissolved in THF(50 ml) and was added with 1,1'-carbonyl diimidazole (2 mmol) at 0° C. The reaction mixture was stirred at room temperature for 4 h, followed by the addition of excess ammonium hydroxide (10 ml) at 0° C. After 5 h stirring at room temperature, water was added to terminate the reaction. The organic layer was extracted 3 times with dichloromethane, dried and concentrated in vacuo. The residue was purified by column chromatography (ethyl acetate:hexane=1:2). The resulting carbamic acid 2-[4-(4-fluoro-benzoyl)-piperidin-1-yl]-1-phenyl-ethyl ester was dissolved in THF and the solution was treated with a solution of HCl in ethyl ether. The resulting precipitate was filtered to give carbamic acid 2-[4-(4-fluoro-benzoyl)-piperidin-1-yl]-1-phenyl-ethyl ester; hydrochloride.

1H-NMR (DMSO-d6, 200 MHz) δ10.9(br, 1H), 8.1(m, 2H), 7.4(m, 7H), 6.8(br, 2H), 6.0(d, 1H), 3.4(m, 7H), 2.0(m, 4H)

EXAMPLE 2

(S)-Carbamic acid 2-[4-(4-fluoro-benzoyl)-piperidin-1-yl]-1-phenyl-ethyl ester; hydrochloride The procedure given in Example 1 was followed using (S)-styrene oxide as a reactant, instead of styrene oxide, to give (S)-carbamic acid 2-[4-(4-fluoro-benzoyl)-piperidin-1-yl]-1-phenyl-ethyl ester; hydrochloride.

1H-NMR (DMSO-d6, 200 MHz) δ10.9(br, 1H), 8.1(m, 2H), 7.4(m, 7H), 6.8(br, 2H), 6.0(d, 1H), 3.4(m, 7H), 2.0(m, 4H)

EXAMPLE 3

(R)-Carbamic acid 2-[4-(4-fluoro-benzoyl)-piperidin-1-yl]-1-phenyl-ethyl ester; hydrochloride The procedure given in Example 1 was followed using (R)-styrene oxide as a reactant, instead of styrene oxide, to give (R)-carbamic acid 2-[4-(4-fluoro-benzoyl)-piperidin-1-yl]-1-phenyl-ethyl ester; hydrochloride.

1H-NMR (DMSO-d6, 200 MHz) δ10.9(br, 1H), 8.1(m, 2H), 7.4(m, 7H), 6.8(br, 2H), 6.0(d, 1H), 3.4(m, 7H), 2.0(m, 4H)

EXAMPLE 4

Carbamic acid 1-(3-chloro-phenyl)-2-[4-(4-fluoro-benzoyl)-piperidin-1-yl]-ethyl ester; hydrochloride The procedure given in Example 1 was followed using 3-chlorostyrene oxide as a reactant, instead of styrene oxide, to give carbamic acid 1-(3-chloro-phenyl)-2-[4-(4-fluoro-benzoyl)-piperidin-1-yl]-ethyl ester; hydrochloride.

1H-NMR (DMSO-d6, 200 MHz) δ10.6(br, 1H), 8.1(m, 2H), 7.4(m, 7H), 6.85(br, 2H), 6.0(d, 1H), 3.4(m, 7H), 2.0(m, 4H)

EXAMPLE 5

Carbamic acid 1-(3,4-dichloro-phenyl)-2-[4-(4-fluoro-benzoyl)-piperidin-1-yl]-ethyl ester; hydrochloride The procedure given in Example 1 was followed using 3,4-dichlorostyrene oxide as a reactant, instead of styrene oxide, to give carbamic acid 1-(3,4-dichloro-phenyl)-2-[4-(4-fluoro-benzoyl)-piperidin-1-yl]-ethyl ester; hydrochloride.

1H-NMR (DMSO-d6, 200 MHz) δ10.7(br, 1H), 8.1(m, 2H), 7.7(m, 2H), 7.4(m, 3H), 6.9(br, 2H), 6.0(d, 1H), 3.4(m, 7H), 2.0(m, 4H)

EXAMPLE 6

Benzyl-carbamic acid 2-[4-(4-fluoro-benzoyl)-piperidin-1-yl]-1-phenyl-ethyl ester; hydrochloride The procedure given in Example 1 was followed using benzyl amine as a reactant, instead of ammonium hydroxide, to give benzyl-carbamic acid 2-[4-(4-fluoro-benzoyl)-piperidin-1-yl]-1-phenyl-ethyl ester; hydrochloride.

1H-NMR (DMSO-d6, 200 MHz) δ9.5(br, 1H), 8.1(m, 3H), 7.3.(m, 12H), 6.0(d, 1H), 3.6(m, 9H), 2.0(m, 4H)

EXAMPLE 7

Carbamic acid 2-[4-(4-fluoro-benzoyl)-piperidin-1-yl]-1-(3-nitro-phenyl)-ethyl ester; hydrochloride The procedure given in Example 1 was followed using 3-nitrostyrene oxide as a reactant, instead of styrene oxide, to give carbamic acid 2-[4-(4-fluoro-benzoyl)-piperidin-1-yl]-1-(3-nitro-phenyl)-ethyl ester; hydrochloride.

1H-NMR (DMSO-d6, 200 MHz) δ10.8(br, 1H), 8.2(m, 4H), 7.8(m, 2H), 7.4(m, 2H), 6.95(br, 2H), 6.2(d, 1H), 3.6(m, 7H), 2.0(m, 4H)

EXAMPLE 8

Carbamic acid 2-[4-(4-fluoro-benzoyl)-piperidin-1-yl]-1-(4-trifluoromethyl-phenyl)-ethyl ester; hydrochloride The procedure given in Example 1 was followed using 4-trifluoromethylstyrene oxide as a reactant, instead of styrene oxide, to give carbamic acid 2-[4-(4-fluoro-benzoyl)-piperidin-1-yl]-1-(4-trifluoromethyl-phenyl)-ethyl ester; hydrochloride.

1H-NMR (DMSO-d6, 200 MHz) δ10.8(br, 1H), 8.15(m, 2H), 7.8(d, 2H), 7.65(d, 2H), 7.4(m, 2H), 6.9(br, 2H), 6.15(d, 1H), 3.5(m, 7H), 2.0(m, 4H)

EXAMPLE 9

Carbamic acid 2-[4-(4-fluoro-benzoyl)-piperidin-1-yl]-1-(4-fluoro-phenyl)-ethyl ester; hydrochloride The procedure given in Example 1 was followed using 4-fluorostyrene oxide as a reactant, instead of styrene oxide, to give carbamic acid 2-[4-(4-fluoro-benzoyl)-piperidin-1-yl]-1-(4-fluoro-phenyl)-ethyl ester; hydrochloride.

1H-NMR (DMSO-d6, 200 MHz) δ10.45(br, 1H), 8.1(m, 2H), 7.35(m, 6H), 6.8(br, 2H), 6.0(d, 1H), 3.4(m, 7H), 2.0(m, 4H)

EXAMPLE 10

Carbamic acid 1-(4-chloro-phenyl)-2-[4-(4-fluoro-benzoyl)-piperidin-1-yl]-ethyl ester; hydrochloride The procedure given in Example 1 was followed using 4-chlorostyrene oxide as a reactant, instead of styrene oxide, to give carbamic acid 1-(4-chloro-phenyl)-2-[4-(4-fluoro-benzoyl)-piperidin-1-yl]-ethyl ester; hydrochloride.

1H-NMR (DMSO-d6, 200 MHz) δ0.5(br, 1H), 8.1(m, 2H), 7.4(m, 6H), 6.8(br, 2H), 6.0(d, 1H), 3.4(m, 7H), 2.0(m, 4H)

EXAMPLE 11

(S)-Carbamic acid 1-(4-chloro-phenyl)-2-[4-(4-fluoro-benzoyl)-piperidin-1-yl]-ethyl ester; hydrochloride The procedure given in Example 1 was followed using (S)-4-chlorostyrene oxide as a reactant, instead of styrene oxide, to give (S)-carbamic acid 1-(4-chloro-phenyl)-2-[4-(4-fluoro-benzoyl)-piperidin-1-yl]-ethyl ester; hydrochloride.

1H-NMR (DMSO-d6, 200 MHz) δ10.5(br, 1H), 8.1(m, 2H), 7.4(m, 6H), 6.8(br, 2H), 6.0(d, 1H), 3.4(m, 7H), 2.0(m, 4H)

EXAMPLE 12

(R)-Carbamic acid 1-(4-chloro-phenyl)-2-[4-(4-fluoro-benzoyl)-piperidin-1-yl]-ethyl ester; hydrochloride The procedure given in Example 1 was followed using (R)-4-chlorostyrene oxide as a reactant, instead of styrene oxide, to give (R)-carbamic acid 1-(4-chloro-phenyl)-2-[4-(4-fluoro-benzoyl)-piperidin-1-yl]-ethyl ester; hydrochloride.

1H-NMR (DMSO-d6, 200 MHz) δ10.5(br, 1H), 8.1(m, 2H), 7.4(m, 6H), 6.8(br, 2H), 6.0(d, 1H), 3.4(m, 7H), 2.0(m, 4H)

EXAMPLE 13

Carbamic acid 1-(2-chloro-phenyl)-2-[4-(4-fluoro-benzoyl)-piperidin-1-yl]-ethyl ester; hydrochloride The procedure given in Example 1 was followed using 2-chlorostyrene oxide as a reactant, instead of styrene oxide, to give carbamic acid 1-(2-chloro-phenyl)-2-[4-(4-fluoro-benzoyl)-piperidin-1-yl]-ethyl ester; hydrochloride.

1H-NMR (DMSO-d6, 200 MHz) δ10.5(br, 1H), 8.1(m, 2H), 7.4(m, 6H), 6.9(br, 2H), 6.2(d, 1H), 3.5(m, 7H), 2.0(m, 4H)

EXAMPLE 14

Carbamic acid 1-(2,4-dichloro-phenyl)-2-[4-(4-fluoro-benzoyl)-piperidin-1-yl]-ethyl ester; hydrochloride The procedure given in Example 1 was followed using 2,4-dichlorostyrene oxide as a reactant, instead of styrene oxide, to give carbamic acid 1-(2,4-dichloro-phenyl)-2-[4-(4-fluoro-benzoyl)-piperidin-1-yl]-ethyl ester; hydrochloride.

1H-NMR (DMSO-d6, 200 MHz) δ11.2(br, 1H), 8.0(m, 2H), 7.3(m, 3H), 7.1(s, 2H), 6.5(br, 2H), 6.2(d, 1H), 3.4(m, 7H), 2.0(m, 4H)

EXAMPLE 15

Carbamic acid 2-[4-(4-fluoro-benzoyl)-piperidin-1-yl]-1-o-tolyl-ethyl ester

The procedure given in Example 1 was followed using 2-methylstyrene oxide as a reactant, instead of styrene oxide, to give carbamic acid 2-[4-(4-fluoro-benzoyl)-piperidin-1-yl]-1-o-tolyl-ethyl ester.

1H-NMR (CDCl3, 200 MHz) δ7.95(m, 2H), 7.35(m, 1H), 7.15(m, 5H), 6.1(d, 1H), 4.85(br, 2H), 3.0(m, 4H), 2.5(dd, 1H), 2.4(s, 3H), 2.3(m, 2H), 1.8(m, 4H)

EXAMPLE 16

Carbamic acid 2-[4-(4-fluoro-benzoyl)-piperidin-1-yl]-1-p-tolyl-ethyl ester

The procedure given in Example 1 was followed using 4-methylstyrene oxide as a reactant, instead of styrene oxide, to give carbamic acid 2-[4-(4-fluoro-benzoyl)-piperidin-1-yl]-1-p-tolyl-ethyl ester.

1H-NMR (CDCl3, 200 MHz) δ7.95(m, 2H), 7.2(m, 6H), 5.85(dd, 1H), 4.7(br, 2H), 3.0(m, 4H), 2.6(dd, 1H), 2.35(s, 3H), 2.25(m, 2H), 1.8(m, 4H)

EXAMPLE 17

Carbamic acid 2-[4-(4-fluoro-benzoyl)-piperidin-1-yl]-1-(4-nitro-phenyl)-ethyl ester The procedure given in Example 1 was followed using 4-nitrostyrene oxide as a reactant, instead of styrene oxide, to give carbamic acid 2-[4-(4-fluoro-benzoyl)-piperidin-1-yl]-1-(4-nitro-phenyl)-ethyl ester.

1H-NMR (CDCl3, 200 MHz) δ8.2(d, 21H), 7.95(m, 2H), 7.5(d, 2H), 7.1(m, 2H), 5.85(dd, 1H), 4.75(br, 2H), 3.0(m, 4H), 2.6(dd, 1 H), 2.3(m, 2H), 1.8(m, 4H)

EXAMPLE 18

Carbamic acid 1-(4-tert-butyl-phenyl)-2-[4-(4-fluoro-benzoyl)-piperidin-1-yl]-ethyl ester The procedure given in Example 1 was followed using 4-tert-butylstyrene oxide as a reactant, instead of styrene oxide, to give carbamic acid 1-(4-tert-butyl-phenyl)-2-[4-(4-fluoro-benzoyl)-piperidin-1-yl]-ethyl ester.

1H-NMR (CDCl3, 200 MHz) δ8.0(d, 2H), 7.35(m, 4H), 7.15(m, 2H), 5.85(dd, 1H), 4.95(s, 2H), 3.1(m, 4H), 2.6(dd, 1H), 2.3(m, 2H), 1.85(m, 4H)

EXAMPLE 19

Carbamic acid 2-[4-(4-fluoro-benzoyl)-piperidin-1-yl]-1-naphthalen-2-yl-ethyl ester The procedure given in Example 1 was followed using 2-naphthalene oxide as a reactant, instead of styrene oxide, to give carbamic acid 2-[4-(4-fluoro-benzoyl)-piperidin-1-yl]-1-naphthalen-2-yl-ethyl ester.

1H-NMR (DMSO-d6, 200 MHz) δ11.2(br, 1H), 7.95(m, 6H), 7.5(m, 3H), 7.3(m, 2H), 6.6(br, 2H), 5.85(d, 1H), 2.95(m, 2H), 2.8(dd, 1H), 2.6(dd, 1H), 2.5(s, 1H), 2.35(m, 2H), 1.6(m, 4H)

EXAMPLE 20

Carbamic acid 2-(4-benzoyl-piperidin-1-yl)-1-(2-chloro-phenyl)-ethyl ester; hydrochloride The procedure given in Example 1 was followed using 2-chlorostyrene oxide and 4-benzoylpiperidine as reactants, instead of styrene oxide and 4-(4-fluorobenzoyl)piperidine, to give carbamic acid 2-(4-benzoyl-piperidin-1-yl)-1-(2-chloro-phenyl)-ethyl ester; hydrochloride.

1H-NMR (DMSO-d6, 200 MHz) δ11.05(br, 1H), 7.90(m, 2H), 7.45(m, 4H), 7.3(m, 2H), 6.5(br, 2H), 6.25(d, 1H), 3.4(m, 7H), 2.0(m, 4H)

EXAMPLE 21

Carbamic acid 1-(2-chloro-phenyl)-2-[4-(4-methoxy-benzyl)-piperidin-1-yl]-ethyl ester; hydrochloride The procedure given in Example 1 was followed using 2-chlorostyrene oxide and 4-(4-methoxybenzoyl)piperidine as reactants, instead of styrene oxide and 4-(4-fluorobenzoyl)piperidine, to give carbamic acid 1-(2-chloro-phenyl)-2-[4-(4-methoxy-benzoyl)-piperidin-1-yl]-ethyl ester; hydrochloride.

1H-NMR (DMSO-d6, 200 MHz) δ10.8(br, 1H), 8.0(m, 2H), 7.4(m, 4H), 7.0(m, 2H), 6.85(br, 2H), 6.2(d, 1H), 3.8(s, 3H), 3.4(m, 7H), 2.0(m, 4H)

EXAMPLE 22

Carbamic acid 2-[4-(4-tert-butyl-benzoyl)-piperidin-1-yl]-1-(2-chloro-phenyl)-ethyl ester The procedure given in Example 1 was followed using 2-chlorostyrene oxide and 4-(4-tert-butylbenzoyl)piperidine as reactants, instead of styrene oxide and 4-(4-fluorobenzoyl)piperidine, to give carbamic acid 2-[4-(4-tert-butyl-benzoyl)-piperidin-1-yl]-1-(2-chloro-phenyl)-ethyl ester.

1H-NMR (CDCl3, 200 MHz) δ7.9(d, 2H), 7.45(m, 3H), 7.3(m, 3H), 6.25(dd, 1H), 5.0(s, 2H), 3.2(m, 2H), 2.95(dd, 1H), 2.8(dd, 1H), 2.65(dd, 1H), 2.3(m, 2H), 1.8(m, 4H), 1.35(s, 9H)

EXAMPLE 23

Carbamic acid 2-[4-(4-chloro-benzoyl)-piperidin-1-yl]-1-(2-chloro-phenyl)-ethyl ester; hydrochloride The procedure given in Example 1 was followed using 2-chlorostyrene oxide and 4-(4-chlorobenzoyl)piperidine as reactants, instead of styrene oxide and 4-(4-fluorobenzoyl) piperidine, to give carbamic acid 2-[4-(4-chloro-benzoyl)-piperidin-1-yl]-1-(2-chloro-phenyl)-ethyl ester; hydrochloride.

1H-NMR (CD3OD, 200 MHz) δ8.0(d, 2H), 7.45(m, 6H), 6.4(d, 1H), 5.9(br, 2H), 3.6(m, 7H), 2,15(m, 4H)

EXAMPLE 24

Azepane-1-carboxylic acid 1-[4-(4-fluoro-benzoyl)-piperidin-1-ylmethyl]-2-phenoxy-ethyl ester The procedure given in Example 24 was followed using hexamethyleneimine as a reactant, instead of ammonium hydroxide, to give azepane-1-carboxylic acid 1-[4-(4-fluoro-benzoyl)-piperidin-1-ylmethyl]-2-phenoxy-ethyl ester.

1H-NMR (CDCl3, 200 MHz) δ7.97(dd, 2H), 7.18(m, 4H), 6.86(dd, 2H), 5.2(m, 1H), 4.18(m, 2H), 3.4(m, 4H), 3.2(m, 1H), 3.04(m, 2H), 2.7(d, 2H), 2.3(m, 2H), 1.8(m, 4H), 1.6(m, 8H)

EXAMPLE 25

Carbamic acid 1-[4-(4-fluoro-benzoyl)-piperidin-1-ylmethyl]-3-phenyl-propyl ester The procedure given in Example 1 was followed using 2-phenethyl-oxirane as a reactant, instead of styrene oxide, to give carbamic acid 1-[4-(4-fluoro-benzoyl)-piperidin-1-ylmethyl]-3-phenyl-propyl ester.

1H-NMR (CDCl3, 200 MHz) δ7.95(dd, 2H), 7.15(m, 7H), 5.17(s, 2H), 4.95(m, 1H), 3.15(m, 1H), 2.98(m, 2H), 2.65(m, 2H), 2.55(dd, 1H), 2.4(dd, 1H), 2.16(m, 2H), 1.85 (m, 6H)

EXAMPLE 26

Piperidine-1-carboxylic acid 1-[4-(4-fluoro-benzoyl)-piperidin-1-ylmethyl]-3-phenyl-propyl ester The procedure given in Example 1 was followed using 2-phenethyl-oxirane and piperidine as reactants, instead of styrene oxide and ammonium hydroxide, to give piperidine-1-carboxylic acid 1-[4-(4-fluoro-benzoyl)-piperidin-1-ylmethyl]-3-phenyl-propyl ester.

1H-NMR (CDCl3, 200 MHz) δ7.95(dd, 2H), 7.15(m, 7H), 4.95(m, 1H), 3.4(s, 4H), 3.15(m, 1H), 2.98(m, 2H), 2.65(m, 2H), 2.55(dd, 1H), 2.45(dd, 1H), 2.2(m, 2H), 1.95 (m, 2H), 1.8(m, 4H), 1.57(m, 6H)

EXAMPLE 27

Carbamic acid 1-[4-(4-fluoro-benzoyl)-piperidin-1-ylmethyl]-2-phenoxy-ethyl ester; hydrochloride A mixture of 4-(4-fluorobenzoyl)piperidine (5 mmol) and 1,2-epoxy-3-phenoxypropane (5 mmol) was refluxed in 30 ml of isopropanol for 4 h. This solution was then concentrated on a rotary evaporator and diluted with ethyl acetate. This mixture was then washed with brine, the resulting organic layer was dried and concentrated in vacuo to give a solid. This was recrystallized in a solution mixture of n-hexane and ethyl acetate to give a white solid. This was dissolved in THF (50 ml) and was added with 1,1'-carbonyl diimidazole (10 mmol) at 0° C. The reaction mixture was stirred at room temperature for 4 h, followed by the addition of excess ammonium hydroxide (10 ml) at 0° C. After 5 h stirring at room temperature, water was added to terminate the reaction. The organic layer was extracted 3 times with dichloromethane, dried and concentrated in vacuo. The residue was purified by column chromatography (ethyl acetate:hexane=1:2). The resulting carbamic acid 1-[4-(4-fluoro-benzoyl)-piperidin-1-ylmethyl]-2-phenoxy-ethyl ester was dissolved in THF and the solution was treated with a solution of HCl in ethyl ether. The resulting precipitate was filtered to give carbamic acid 1-[4-(4-fluoro-benzoyl)-piperidin-1-ylmethyl]-2-phenoxy-ethyl ester; hydrochloride.

1H-NMR (DMSO-d6, 200 MHz) δ10.3(br, 1H), 8.1(m, 2H), 7.35(m, 4H), 6.95(m, 3H), 6.85(br, 2H), 5.35(m, 1H), 4.15(m, 2H), 3.5(m, 7H), 2.0(m, 4H)

EXAMPLE 28

Carbamic acid 2-(4-chloro-phenoxy)-1-[4-(4-fluoro-benzoyl)-piperidin-1-ylmethyl]-ethyl ester The procedure given in Example 27 was followed using 4-chlorophenyl glycidyl ether as a reactant, instead of 1,2-epoxy-3-phenoxypropane, to give carbamic acid 2-(4-chloro-phenoxy)-1-[4-(4-fluoro-benzoyl)-piperidin-1-ylmethyl]-ethyl ester.

1H-NMR (CDCl3, 200 MHz) δ7.9(dd, 2H), 7.15(m, 4H), 6.8(d, 2H), 5.9(br, 2H), 5.1(m, 1H), 4.1(m, 2H), 3.2(m, 1H), 3.0(m, 2H), 2.7(d, 2H), 2.3(m, 2H), 1.75(m, 4H)

EXAMPLE 29

Carbamic acid 1-[4-(4-fluoro-benzoyl)-piperidin-1-ylmethyl]-2-(4-methoxy-phenoxy)-ethyl ester The procedure given in Example 27 was followed using glycidyl 4-methoxyphenyl ether as a reactant, instead of 1,2-epoxy-3-phenoxypropane, to give carbamic acid 1-[4-(4-fluoro-benzoyl)-piperidin-1-ylmethyl]-2-(4-methoxy-phenoxy)-ethyl ester.

1H-NMR (CDCl3, 200 MHz) δ7.95(dd, 2H), 7.15(m, 2H), 6.85(m, 4H), 5.15(m, 1H), 5.1(br, 2H), 4.1(m, 2H), 3.75(s, 3H), 3.2(m, 1 H), 3.05(m, 2H), 2.75(d, 2H), 2.35(m, 2H), 1.85(m, 4H)

EXAMPLE 30

Carbamic acid 2-(4-tert-butyl-phenoxy)-1-[4-(4-fluoro-benzoyl)-piperidin-1-ylmethyl]-ethyl ester The procedure given in Example 27 was followed using 4-tert-butyl-phenyl glycidyl ether as a reactant, instead of 1,2-epoxy-3-phenoxypropane, to give carbamic acid 2-(4-tert-butyl-phenoxy)-1-[4-(4-fluoro-benzoyl)-piperidin-1-ylmethyl]-ethyl ester 1H-NMR (CDCl3, 200 MHz) δ7.95(dd, 2H), 7.3(d, 2H), 7.15(t, 2H), 6.9(d, 2H), 5.25(br, 2H), 5.2(m, 1H), 4.15(m, 2H), 3.2(m, 1H), 3.05(m, 2H), 2.7(d, 2H), 1.8(m, 4H), 1.3(s, 9H)

EXAMPLE 31

Pyrrolidine-1-carboxylic acid 1-[4-(4-fluoro-benzoyl)-piperidin-1-ylmethyl]-2-phenoxy-ethyl ester The procedure given in Example 27 was followed using pyrrolidine as a reactant, instead of ammonium hydroxide, to give pyrrolidine-1-carboxylic acid 1-[4-(4-fluoro-benzoyl)-piperidin-1-ylmethyl]-2-phenoxy-ethyl ester.

1H-NMR (CDCl3, 200 MHz) δ7.99(dd, 2H), 7.17(m, 4H), 6.86(d, 2H), 5.23(m, 1H), 4.18(m, 2H), 3.35(m, 5H), 3.1(m, 2H), 2.82(d, 2H), 2.45(m, 2H), 1.9(m, 8H)

EXAMPLE 32

Piperidine-1-carboxylic acid 1-[4-(4-fluoro-benzoyl)-piperidin-1-ylmethyl]-2-phenoxy-ethyl ester The procedure given in Example 27 was followed using piperidine as a reactant, instead of ammonium hydroxide, to give piperidine-1-carboxylic acid 1-[4-(4-fluoro-benzoyl)-piperidin-1-ylmethyl]-2-phenoxy-ethyl ester.

1H-NMR (CDCl3, 200 MHz) δ7.99(dd, 2H), 7.18(m, 4H), 6.86(dd, 2H), 5.18(m, 1H), 4.18(m, 2H), 3.4(m, 4H), 3.2(m, 1H), 3.04(m, 2H), 2.7(d, 2H), 2.3(m, 2H), 1.8(m, 4H), 1.55(m, 6H)

EXAMPLE 33

Morpholine-4-carboxylic acid 1-[4-(4-fluoro-benzoyl)-piperidin-1-ylmethyl]-2-phenoxy-ethyl ester The procedure given in Example 27 was followed using morpholine as a reactant, instead of ammonium hydroxide, to give morpholine-4-carboxylic acid 1-[4-(4-fluoro-benzoyl)-piperidin-1-ylmethyl]-2-phenoxy-ethyl ester.

1H-NMR (CDCl3, 200 MHz) δ7.98(dd, 2H), 7.2(m, 4H), 6.86(m, 2H), 5.2(m, 1H), 4.18(m, 2H), 3.65(m, 4H), 3.5(m, 4H), 3.2(m, 1H), 3.07(m, 2H), 2.73(d, 2H) 2.36(m, 2H), 1.85(m, 4H)

EXAMPLE 34

(4-Fluoro-phenyl)-{1-[2-methoxy-2-(4-nitro-phenyl)-ethyl]-piperidin-4yl}-methanone; hydrochloride A mixture of 4-(4-fluorobenzoyl)piperidine(5 mmol) and 2-(4-nitro-phenyl)oxirane (5 mmol) was refluxed in 30 ml of isopropanol for 4 h. This solution was then concentrated on a rotary evaporator and diluted with ethyl acetate. This mixture was then washed with brine, the resulting organic layer was dried and concentrated in vacuo. The crude product was dissolved in dichloromethane (50 ml) and was added with methanesulfonyl chloride (2 eq.) and triethylamine (3 eq.) at 0° C. The reaction mixture was stirred at room temperature for 1 h. This solution was then concentrated on a rotary evaporator and dissolved in THF (50 ml), added triethylamine (3 eq.), followed by the addition of excess methanol (>10 eq.). After 12 hours stirring at 80° C., this solution is concentrated on a rotary evaporator and diluted with ethyl acetate. The organic layer was extracted 3 times with dichloromethane, dried and concentrated in vacuo. The residue was purified by column chromatography (ethyl acetate:hexane=1:1). The resulting (4-fluoro-phenyl)-{1-[2-methoxy-2-(4-nitro-phenyl)-ethyl]-piperidin-4-yl}-methanone was dissolved in dichloromethane and the solution was treated with a solution of HCl in ethyl ether. The resulting precipitate was filtered to give (4-fluoro-phenyl)-{1-[2-methoxy-2-(4-nitro-phenyl)-ethyl]-piperidin-4-yl}-methanone; hydrochloride 1H-NMR (DMSO-d6, 200 MHz) δ11.1(br, 1H), 8.2(m, 2H), 8.0(m, 2H), 7.5(m, 2H), 7.2(m, 2H), 4.5(m, 1H), 3.4(s, 3H), 3.2(m, 2H), 2.9(m, 1H), 2.8(m, 1H), 2.5(m, 1H), 2.3(m, 2H), 1.8(m, 4H)

EXAMPLE 35

(S)-(4-Fluoro-phenyl)-{1-[2-methoxy-2-(4-nitro-phenyl)-ethyl]-piperidin-4-yl}-methanone The procedure given in Example 34 was followed using (S)-4-nitrostyrene oxide as a reactant, instead of 2-(4-nitrophenyl)oxirane, to give (S)-(4-fluoro-phenyl)-{1-[2-methoxy-2-(4-nitro-phenyl)-ethyl]-piperidin-4-yl}-methanone.

1H-NMR (CDCl3, 200 MHz) δ8.3(m, 2H), 8.0(m, 2H), 7.5(m, 2H), 7.2(m, 2H), 4.5(m, 1H), 3.5(s, 3H), 3.2(m, 2H), 2.9(m, 1H), 2.8(m, 1H), 2.5(m, 1H), 2.3(m, 2H), 1.8(m, 4H)

EXAMPLE 36

(R)-(4-Fluoro-phenyl)-{1-[2-methoxy-2-(4-nitro-phenyl)-ethyl]-piperidin-4-yl}-methanone The procedure given in Example 34 was followed using (R)-4-nitrostyrene oxide as a reactant, instead of 2-(4-nitro-phenyl)oxirane, to give (R)-(4-fluoro-phenyl)-{1-[2-methoxy-2-(4-nitro-phenyl)-ethyl]-piperidin-4-yl}-methanone.

1H-NMR (CDCl3, 200 MHz) δ8.2(m, 2H), 8.1(m, 2H), 7.7(m, 2H), 7.3(m, 2H), 4.5(m, 1H), 3.4(s, 3H), 3.3(m, 2H), 2.9(m, 1H), 2.8(m, 1H), 2.5(m, 1H), 2.3(m, 2H), 1.8(m, 4H)

EXAMPLE 37

{1-[2-Ethoxy-2-(4-nitro-phenyl)-ethyl]-piperidin-4-yl}-(4-fluoro -1phenyl)-methanone The procedure given in Example 34 was followed using ethanol as a reactant, instead of methanol, to give {1-[2-ethoxy-2-(4-nitro-phenyl)-ethyl]-piperidin-4-yl}-(4-fluoro-phenyl)-methanone.

1H-NMR (CDCl3, 200 MHz) δ8.3(m, 2H), 8.0(m, 2H), 7.7(m, 2H), 7.2(m, 2H), 4.5(m, 1H), 3.4(q, 2H), 3.2(m, 2H), 2.9(m, 1H), 2.8(m, 1H), 2.5(m, 1H), 2.3(m, 2H), 1.8(m, 4H), 1.2(t, 3H)

EXAMPLE 38

(4-Fluoro-phenyl)-{1-[2-isopropoxy-2-(4-nitro-phenyl)-ethyl]-piperidin-4-yl}-methanone The procedure given in Example 34 was followed using isopropanol as a reactant, instead of methanol, to give (4-fluoro-phenyl)-{1-[2-isopropoxy-2-(4-nitro-phenyl)-ethyl]-piperidin-4-yl}-methanone.

1H-NMR (CDCl3, 200 MHz) δ8.2(m, 2H), 8.0(m, 2H), 7.6(m, 2H), 7.1(m, 2H), 4.7(m, 1H), 3.5(m, 1H), 3.2(m, 2H), 2.9(m, 1H), 2.8(m, 1H), 2.5(m, 1H), 2.3(m, 2H), 1.8(m, 4H), 1.1(dd, 6H)

EXAMPLE 39

{1-[2-Cyclopentyloxy-2-(4-nitro-phenyl)-ethyl]-piperidin-4-yl}-(4-fluoro-phenyl)-methanone The procedure given in Example 34 was followed using cyclopentanol as a reactant, instead of methanol, to give {1-[2-cyclopentyloxy-2-(4-nitro-phenyl)-ethyl]-piperidin-4-yl}-(4-fluoro-phenyl)-methanone.

1H-NMR (CDCl3, 200 MHz) δ8.2(m, 2H), 8.0(m, 2H), 7.5(m, 2H), 7.1(m, 2H), 4.6(m, 1H), 3.8(m, 1H), 3.2(m, 2H), 2;9(m, 1H), 2.8(m, 1H), 2.5(m, 1H), 2.3(m, 2H), 1.7(br, 14H)

EXAMPLE 40

{1-[2-Benzyloxy-2-(4-nitro-phenyl)-ethyl]-piperidin-4-yl}-(4-fluoro-phenyl)-methanone The procedure given in Example 34 was followed using benzyl alcohol as a reactant, instead of methanol, to give {1-[2-benzyloxy-2-(4-nitro-phenyl)-ethyl]-piperidin-4-yl}-(4-fluoro-phenyl)-methanone.

1H-NMR (CDCl3, 200 MHz) δ8.3(m, 2H), 8.0(m, 2H), 7.6(m, 2H), 7.3(m, 5H), 7.1(m, 2H), 4.7(m, 2H), 4.4(m, 1H), 3.2(m, 2H), 2.9(m, 2H), 2.5(m, 1H), 2.4(m 1.8(m, 4H)

EXAMPLE 41

{1-[2-(4-Ethyl-phenyl)-2-methoxy-ethyl]-piperidin-4-yl}-(4-fluoro-phenyl)-methanone The procedure given in Example 34 was followed using 4-ethylstyrene oxide as a reactant, instead of 2-(4-nitro-phenyl)oxirane, to give {1-[2-(4-ethyl-phenyl)-2-methoxy-ethyl]-piperidin-4-yl}-(4-fluoro-phenyl)-methanone.

1H-NMR (CDCl3, 200 MHz) δ8.0(m, 2H), 7.2(m, 6H), 4.4(m, 1H), 3.3(s, 3H), 3.1(m, 3H), 2.8(m, 1H), 2.7(q, 2H), 2.5(m, 1H), 2.3(m, 2H), 1.8(m, 4H), 1.2(t, 3H).

EXAMPLE 42

(S)-{1-[2-(4-Ethyl-phenyl)-2-methoxy-ethyl]-piperidin-4-yl}-(4-fluoro-phenyl)-methanone The procedure given in Example 34 was followed using (S)-4-ethylstyrene oxide as a reactant, instead of 2-(4-nitro-phenyl)oxirane, to give (S)-{1-[2-(4-ethyl-phenyl)-2-methoxy-ethyl]-piperidin-4-yl}-(4-fluoro-phenyl)-methanone.

1H-NMR (CDCl3, 200 MHz) δ8.0(m, 2H), 7.2(m, 6H), 4.4(m, 1H), 3.3(s, 3H), 3.1(m, 3H), 2.8(m, 1H), 2.7(q, 2H), 2.5(m, 1H), 2.3(m, 2H), 1.8(m, 4H), 1.2(t, 3H).

EXAMPLE 43

(4-Fluoro-phenyl)-{1-[2-(4-isopropyl-phenyl)-2-methoxy-ethyl]-piperidin-4-yl}-methanone The procedure given in Example 34 was followed using 4-isopropylstyrene oxide as a reactant, instead of 2-(4-nitro-phenyl)oxirane, to give (4-fluoro-phenyl)-{1-[2-(4-isopropyl-phenyl)-2-methoxy-ethyl]-piperidin-4-yl}-methanone.

1H-NMR (CDCl3, 200 MHz) δ8.0(m, 2H), 7.2(m, 6H), 4.4(m, 1H), 3.3(s, 3H), 3.2(m, 3H), 2.9(m, 2H), 2.5(m, 1H), 2.3(m, 2H), 1.8(m, 4H)

EXAMPLE 44

(S)-(4-Fluoro-phenyl)-{1-[2-(4-isopropyl-phenyl)-2-methoxy-ethyl]-piperidin-4-yl}-methanone The procedure given in Example 34 was followed using (S)-4-isopropylstyrene oxide as a reactant, instead of 2-(4-nitro-phenyl)oxirane, to give (S)-(4-fluoro-phenyl)-{1-[2-(4-isopropyl-phenyl)-2-methoxy-ethyl]-piperidin-4-yl}-methanone.

1H-NMR (CDCl3, 200 MHz) δ8.0(m, 2H), 7.2(m, 6H), 4.4(m, 1H), 3.3(s, 3H), 3.2(m, 3H), 2.9(m, 2H), 2.5(m, 1H), 2.3(m, 2H), 1.8(m, 4H)

EXAMPLE 45

(4-Fluoro-phenyl)-[1-(2-methoxy-2-naphthalen-2-yl-ethyl)-piperidin-4-yl]-methanone; hydrochloride The procedure given in Example 34 was followed using 2-naphthalene oxide as a reactant, instead of 2-(4-nitro-phenyl)oxirane, to give (4-fluoro-phenyl)-[1-(2-methoxy-2-naphthalen-2-yl-ethyl)-piperidin-4-yl]-methanone; hydrochloride 1H-NMR (DMSO-d6, 200 MHz) δ10.8(br, 1H), 8.0(m, 2H), 7.9(m, 4H), 7.5(m, 3H), 7.1(m, 2H), 4.5(m, 1H), 3.4(s, 3H), 3.2(m, 4H), 2.9(m, 1H), 2.6(m, 1H), 2.3(m, 1H), 1.8(m, 4H)

EXAMPLE 46

(S)-(4-Fluoro-phenyl)-[1-(2-methoxy-2-naphthalen-2-yl-ethyl)-piperidin-4-yl]-methanone; hydrochloride The procedure given in Example 34 was followed using (S)-2-naphthalene oxide as a reactant, instead of 2-(4-nitro-phenyl)oxirane, to give (S)-(4-fluoro-phenyl)-[1-(2-methoxy-2-naphthalen-2-yl-ethyl)-piperidin-4-yl]-methanone; hydrochloride.

1H-NMR (DMSO-d6, 200 MHz) δ10.8(br, 1H), 8.1(m, 2H), 7.9(m, 4H), 7.5(m, 3H), 7.1(m, 2H), 4.5(m, 1H), 3.4(s, 3H), 3.1(m, 4H), 2.9(m, 1H), 2.6(m, 1H), 2.4(m, 1H), 1.8(m, 4H)

EXAMPLE 47

{1-[2-(3,4-Dimethyl-phenyl)-2-methoxy-ethyl]-piperidin-4-yl}-(4-fluoro-phenyl)-methanone The procedure given in Example 34 was followed using 3,4-dimethylstyrene oxide as a reactant, instead of 2-(4-nitro-phenyl)oxirane, to give {-[2-(3,4-dimethyl-phenyl)-2-methoxy-ethyl]-piperidin-4-yl}-(4-fluoro-phenyl)-methanone.

1H-NMR (CDCl3, 200 MHz) δ8.0(m, 2H), 7.1(m, 5H), 4.3(m, 1H), 3.2(m, 6H), 2.9(m, 1H), 2.5(m, 1H), 2.2(m, 8H), 1.8(m, 4H)

EXAMPLE 48

{1-[2-(4-Chloro-phenyl)-2-methoxy-ethyl]-piperidin-4-yl}-(4-fluoro-phenyl)-methanone The procedure given in Example 34 was followed using 4-chlorostyrene oxide as a reactant, instead of 2-(4-nitro-phenyl)oxirane, to give {1-[2-(4-chloro-phenyl)-2-methoxy-ethyl]-piperidin-4-yl}-(4-fluoro-phenyl)-methanone.

1H-NMR (CDCl3, 200 MHz) δ8.0(m, 2H), 7.2(m, 6H), 4.3(m, 1H), 3.3(m, 5H), 2.9(m, 1H), 2.7(m, 1H), 2.4(m, 1H), 2.2(m, 2H), 1.9(m, 4H)

EXAMPLE 49

(4-Fluoro-phenyl)-[1-(2-methoxy-2-thiophen-2-yl-ethyl)-piperidin-4-yl]-methanone The procedure given in Example 34 was followed using 2-thiophen-2-yl-oxirane as a reactant, instead of 2-(4-nitro-phenyl)oxirane, to give (4-fluoro-phenyl)-[1-(2-methoxy-2-thiophen-2-yl-ethyl)-piperidin-4-yl]-methanone.

1H-NMR (CDCl3, 200 MHz) δ8.0(m, 2H), 7.1(m, 5H), 4.6(m, 1H), 3.4(s, 3H), 3.0(m, 6H), 2.4(m, 2H), 1.8(m, 4H)

EXAMPLE 50

(4-Fluoro-phenyl)-{1-[2-methoxy-2-(4-trifluoromethyl-phenyl)-ethyl]-piperidin-4yl}-methanone The procedure given in Example 34 was followed using 4-trifluoromethylstyrene oxide as a reactant, instead of 2-(4-nitro-phenyl)oxirane, to give (4-fluoro-phenyl)-{1-[2-methoxy-2-(4-trifluoromethyl-phenyl)-ethyl]-piperidin-4-yl}-methanone.

1H-NMR (CDCl3, 200 MHz) δ8.0(m, 2H), 7.6(m, 2H), 7.4(m, 2H), 7.1(m, 2H), 4.4(m, 1H), 3.3(s, 3H), 3.0(m, 2H), 2.9(m, 1H), 2.8(m, 1H), 2.5(m, 1H), 2.2(m, 2H), 1.8(m, 4H)

EXAMPLE 51

(4-Fluoro-phenyl)-{1-[2-methoxy-2-(4-methoxy-phenyl)-ethyl]-piperidin-4-yl}-methanone The procedure given in Example 34 was followed using 4-methoxystyrene oxide as a reactant, instead of 2-(4-nitro-phenyl)oxirane, to give (4-fluoro-phenyl)-{1-[2-methoxy-2-(4-methoxy-phenyl)-ethyl]-piperidin-4-yl}-methanone.

1H-NMR (CDCl3, 200 MHz) δ8.0(m, 2H), 7.2(m, 4H), 6.8(m, 2H), 4.3(m, 1H), 3.8(s, 3H), 3.2(s, 3H), 3.1(m, 3H), 2.8(m, 1H), 2.5(m, 1H), 2.3(m, 2H), 1.8(m, 4H)

EXAMPLE 52

4-{2-[4-(4-Fluoro-benzoyl)-piperidin-1-yl]-1-methoxy-ethyl}-benzonitrile

The procedure given in Example 34 was followed using 4-oxiranyl-benzonitrile as a reactant, instead of 2-(4-nitro-phenyl)oxirane, to give 4-{2-[4-(4-fluoro-benzoyl)-piperidin-1-yl]-1-methoxy-ethyl}-benzonitrile.

1H-NMR (CDCl3, 200 MHz) δ8.0(m, 2H), 7.6(m, 2H), 7.4(m, 2H), 7.0(m, 2H), 4.4(m, 1H), 3.0(br, 8H), 2.4(br, 4H), 1.8(m, 3H)

EXAMPLE 53

(4-Fluoro-phenyl)-{1-[2-(4-methanesulfonyl-phenyl)-2-methoxy-ethyl]-piperidin-4yl}-methanone The procedure given in Example 34 was followed using 2-(4-methanesulfonyl-phenyl)-oxirane as a reactant, instead of 2-(4-nitro-phenyl)oxirane, to give (4-fluoro-phenyl)-{1-[2-(4-methanesulfonyl-phenyl)-2-methoxy-ethyl]-piperidin-4-yl}-methanone.

1H-NMR (CDCl3, 200 MHz) δ8.0(m, 4H), 7.5(m, 2H), 7.1(m, 2H), 4.5(m, 1H), 3.4(s, 3H), 3.0(s, 3H), 2.8(m, 3H), 2.5(m, 1H), 2.3(m, 2H), 1.8(m, 4H)

EXAMPLE 54

(4-Fluoro-phenyl)-{1-[2-methoxy-2-(4-trifluoromethoxy-phenyl)-ethyl]-piperidin-4-yl}-methanone The procedure given in Example 34 was followed using 2-(4-trifluoromethoxy-phenyl)-oxirane as a reactant, instead of 2-(4-nitro-phenyl)oxirane, to give (4-fluoro-phenyl)-{1-[2-methoxy-2-(4-trifluoromethoxy-phenyl)-ethyl]-piperidin-4-yl}-methanone.

1H-NMR (CDCl3, 200 MHz) δ8.0(m, 2H), 7.2(m, 61H), 4.4(m, 1H), 3.2(m, 7H), 2.8(m, 1H), 2.5(m, 1H), 2.3(m, 2H), 1.8(m, 4H)

EXAMPLE 55

(4-Fluoro-phenyl)-[1-(2-methoxy-2-pyridin-2-yl-ethyl)-piperidin-4-yl]-methanone

The procedure given in Example 34 was followed using 2-oxiranyl-pyridine as a reactant, instead of 2-(4-nitro-phenyl)oxirane, to give (4-fluoro-phenyl)-[1-(2-methoxy-2-pyridin-2-yl-ethyl)-piperidin-4-yl]-methanone.

1H-NMR (CDCl3, 200 MHz) δ8.4(m, 1H), 7.9(m, 2H), 7.6(m, 1H), 7.3(m, 1H), 7.0(m, 31H), 4.5(m, 1H), 3.0(m, 7H), 2.8(m, 21H), 2.1(m, 21H), 1.8(m, 4H)

EXAMPLE 56

(4-Fluoro-phenyl)-[1-(2-methoxy-2-quinolin-2-yl-ethyl)-piperidin-4-yl]-methanone The procedure given in Example 34 was followed using 2-oxiranyl-quinoline as a reactant, instead of 2-(4-nitrophenyl)oxirane, to give (4-fluoro-phenyl)-[1-(2-methoxy-2-quinolin-2-yl-ethyl)-piperidin-4-yl]-methanone.

1H-NMR (CDCl3, 200 MHz) δ8.2(m, 2H), 8.0(m, 2H), 7.8(m, 2H), 7.6(m, 2H), 7.1(m, 2H), 4.7(m, 1H), 3.4(s, 3H), 3.2(m, 3H), 2.9(m, 1H), 2.7(m, 1H), 2.3(m, 2H), 1.9(m, 4H)

EXAMPLE 57

(4-Chloro-phenyl)-{1-[2-methoxy-2-(4-nitro-phenyl)-ethyl]-piperidin-4-yl}-methanone The procedure given in Example 34 was followed using 4-(4-chlorobenzoyl)piperidine as a reactant, instead of 4-(4-fluorobenzoyl)piperidine, to give (4-chloro-phenyl)-{1-[2-methoxy-2-(4-nitro-phenyl)-ethyl]-piperidin-4-yl}-methanone.

1H-NMR (CDCl3, 200 MHz) δ8.2(m, 2H), 7.8(m, 2H), 7.2(m, 4H), 4.4(m, 1H), 3.3(s, 3H), 3.1(m, 2H), 2.9(m, 1H), 2.8(m, 1H), 2.4(m, 1H), 2.2(m, 2H), 1.8(m, 4H)

EXAMPLE 58

{1-[2-Methoxy-2-(4nitro-phenyl)-ethyl]-piperidin-4-yl}-p-tolyl-methanone

The procedure given in Example 34 was followed using 4-(4-methylbenzoyl)piperidine as a reactant, instead of 4-(4-fluorobenzoyl)piperidine, to give {1-[2-methoxy-2-(4-nitro-phenyl)-ethyl]-piperidin-4-yl}-p-tolyl-methanone.

1H-NMR (CDCl3, 200 MHz) δ8.2(m, 2H), 7.8(m, 2H), 7.4(m, 2H), 7.2(m, 2H), 4.5(m, 1H), 3.3(s, 3H), 3.1(m, 2H), 2.9(m, 1H), 2.8(m, 1H), 2.6(m, 1H), 2.3(m, 2H), 1.8(m, 4H)

EXAMPLE 59

(4-Fluoro-phenyl)-[1-(2-ethoxy-3-phenoxy-propyl)-piperidin-4-yl]-methanone; hydrochloride A mixture of 4-(4-fluorobenzoyl)piperidine (5mmol) and 1,2-epoxy-3-phenoxypropane (5 mmol) was refluxed in 30 ml of isopropanol for 4 h. This solution was then concentrated on a rotary evaporator and diluted with ethyl acetate. This mixture was then washed with brine, the resulting organic layer was dried and concentrated in vacuo. The crude product was dissolved in THF (50 ml) and was added with sodium hydride (2 eq.) at 0° C. The reaction mixture was stirred at room temperature for 10 min. This solution was followed by the addition of excess iodoethane (>3 eq.). After 1 hour stirring at 25° C., this solution is concentrated on a rotary evaporator and diluted with ethyl acetate. The organic layer was extracted 3 times with dichloromethane, dried and concentrated in vacuo. The residue was purified by column chromatography (ethyl acetate:hexane=1:1). The resulting (4-fluoro-phenyl)-[1-(2-ethoxy-3-phenoxy-propyl)-piperidin-4-yl]-methanone was dissolved in dichloromethane and the solution was treated with a solution of HCl in ethyl ether.

The resulting precipitate was filtered to give (4-fluorophenyl)-[1-(2-ethoxy-3-phenoxy-propyl)-piperidin-4-yl]-methanone; hydrochloride.

1H-NMR (CDCl3, 200 MHz) δ12.0(br, 1H), 8.0(m, 2H), 7.2(m, 4H), 6.8(m, 3H), 4.7(m, 2H), 4.2(m, 2H), 3.8(m, 4H), 3.3(m, 6H), 2.6(m, 3H), 2.2(m, 2H)

EXAMPLE 60

(4-Fluoro-phenyl)-[1-(2-methoxy-3-phenoxy-propyl)-piperidin-4-yl]-methanone

The procedure given in Example 59 was followed using iodomethane as a reactant, instead of iodoethane, to give (4-fluoro-phenyl)-[1-(2-methoxy-3-phenoxy-propyl)-piperidin-4-yl]-methanone.

1H-NMR (CDCl3, 200 MHz) δ8.0(m, 2H), 7.3(m, 2H), 7.1(m, 2H), 6.9(m, 3H), 4.2(m, 2H), 3.7(m, 1H), 3.5(m, 3H), 3.2(m, 1H), 3.0(m,2H), 2.6(m, 2H), 2.2(m, 2H), 1.8(m, 4H)

EXAMPLE 61

(S)-(4-Fluoro-phenyl)-[1-(2-methoxy-3-phenoxy-propyl)-piperidin-4-yl]-methanone

The procedure given in Example 59 was followed using (S)-1,2-epoxy-3-phenoxypropane and iodomethane as reactants, instead of 1,2-epoxy-3-phenoxypropane and iodoethane, to give (S)-(4-fluoro-phenyl)-[1-(2-methoxy-3-phenoxy-propyl)-piperidin-4-yl]-methanone.

1H-NMR (CDCl3, 200 MHz) δ8.0(m, 2H), 7.3(m, 2H), 7.1(m, 2H), 6.9(m, 3H), 4.2(m, 2H), 3.7(m, 1H), 3.5(m, 3H), 3.2(m, 1H), 3.0(m,2H), 2.6(m, 2H), 2.2(m, 2H), 1.8(m, 4H)

EXAMPLE 62

(R)-(4-Fluoro-phenyl)-[1-(2-methoxy-3-phenoxy-propyl)-piperidin-4-yl]-methanone

The procedure given in Example 59 was followed using (R)-1,2-epoxy-3-phenoxypropane and iodomethane as reactants, instead of 1,2-epoxy-3-phenoxypropane and iodoethane, to give (R)-(4-fluoro-phenyl)-[1-(2-methoxy-3-phenoxy-propyl)-piperidin-4-yl]-methanone.

1H-NMR (CDCl3, 200 MHz) δ8.0(m, 2H), 7.3(m, 2H), 7.1(m, 2H), 6.9(m, 3H), 4.2(m, 2H), 3.7(m, 1H), 3.5(m, 3H), 3.2(m, 1H), 3.0(m, 2H), 2.6(m, 2H), 2.2(m, 2H), 4H)

EXAMPLE 63

(4-Fluoro-phenyl)-[1-(2-methoxy-3-(4-chloro-phenoxy)-propyl)-piperidin-4-yl]-methanone The procedure given in Example 59 was followed using 4-chlorophenyl glycidyl ether and iodomethane as reactants, instead of 1,2-epoxy-3-phenoxypropane and iodoethane, to give (4-fluoro-phenyl)-[1-(2-methoxy-3-(4-chloro-phenoxy)-propyl)-piperidin-4-yl]-methanone.

1H-NMR (CDCl3, 200 MHz) 8.2(m, 2H), 8.0(m, 2H), 7.5(m, 2H), 7.2(m, 2H), 4.5(m, 1H), 3.4(s, 3H), 3.2(m, 2H), 2.9(m, 1H), 2.8(m, 1H), 2.5(m, 1H), 2.3(m, 2H), 1.8(m, 4H)

EXAMPLE 64

(4-Fluoro-phenyl)-[1-(2-methoxy-3-(4-methoxy-phenoxy)-propyl)-piperidin-4-yl]-methanone The procedure given in Example 59 was followed using glycidyl 4-methoxyphenyl ether and iodomethane as reactants, instead of 1,2-epoxy-3-phenoxypropane and iodoethane, to give (4-fluoro-phenyl)-[1-(2-methoxy-3-(4-methoxy-phenoxy)-propyl)-piperidin-4-yl]-methanone.

1H-NMR (CDCl3, 200 MHz) δ8.0(m, 2H), 7.2(m, 2H), 6.8(m, 4H), 4.0(m, 1H), 3.8(s, 3H), 3.7(m, 1H), 3.6(s, 3H), 3.0(m, 2H), 2.8(m, 3H), 2.2(m, 3H), 1.8(m, 4H)

EXAMPLE 65

(4-Fluoro-phenyl)-[1-(2-methoxy-3-(2-methyl-phenoxy)-propyl)-piperidin-4-yl]-methanone The procedure given in Example 59 was followed using glycidyl 2-methylphenyl ether and iodomethane as reactants, instead of 1,2-epoxy-3-phenoxypropane and iodoethane, to give (4-fluoro-phenyl)-[1-(2-methoxy-3-(2-methyl-phenoxy)-propyl)-piperidin-4-yl]-methanone.

1H-NMR (CDCl3, 200 MHz) δ8.0(m, 2H), 7.2(m, 4H), 6.9(m, 2H), 4.1(m, 3H), 3.8(m, 2H), 3.5(m, 3H), 3.2(m, 1H), 3.0(m,2H), 2.6(m, 4H), 2.2(m, 1H), 1.8(m, 4H)

EXAMPLE 66

(4-Fluoro-phenyl)-[1-(2-methoxy-3-(4-tert-butyl-phenoxy)-propyl)-piperidin-4-yl]-methanone The procedure given in Example 59 was followed using 4-tert-butylphenyl glycidyl ether and iodomethane as reactants, instead of 1,2-epoxy-3-phenoxypropane and iodoethane, to give (4-fluoro-phenyl)-[1-(2-methoxy-3-(4-tert-butyl-phenoxy)-propyl)-piperidin-4-yl]-methanone.

1H-NMR (CDCl3, 200 MHz) δ8.0(m, 2H), 7.3(m, 2H), 7.2(m, 2H), 6.9(m, 2H), 4.1(m, 3H), 3.8(m, 1H), 3.5(s, 3H), 3.1(m, 2H), 2.6(m, 2H), 2.3(m, 2H), 1.8(m, 4H), 1.3(m, 9H)

EXAMPLE 67

(4Fluoro-phenyl)-[1-(2-methoxy-3-(4-nitro-phenoxy)-propyl)-piperidin-4yl]-methanone The procedure given in Example 59 was followed using 4-nitrophenyl glycidyl ether and iodomethane as reactants, instead of 1,2-epoxy-3-phenoxypropane and iodoethane, to give (4-fluoro-phenyl)-[1-(2-methoxy-3-(4-nitro-phenoxy)-propyl)-piperidin-4-yl]-methanone.

1H-NMR (CDCl3, 200 MHz) δ8.2(m, 2H), 8.0(m, 2H), 7.2(m, 4H), 4.2(m, 2H), 3.8(m, 1H), 3.5(s, 3H), 3.2(m, 1H), 3.0(m,2H), 2.6(m, 2H), 2.3(m, 2H), 1.8(m, 4H)

EXAMPLE 68

(4-Fluoro-phenyl)-[1-(2-propyloxy-3-phenoxy-propyl)-piperidin-4-yl]-methanone; hydrochloride The procedure given in Example 59 was followed using iodopropane as a reactant, instead of iodoethane, to give (4-fluoro-phenyl)-[1-(2-propyloxy-3-phenoxy-propyl)-piperidin-4-yl]-methanone; hydrochloride.

1H-NMR (CDCl3, 200 MHz) δ12.4(br, 1H), 8.0(m, 2H), 7.3(m, 4H), 6.9(m, 3H), 4.7(m, 1H), 4.1(m, 3H), 3.7(m, 4H), 3.3(m, 4H), 2.8(m,2H), 2.1(m, 4H), 1.0(m, 3H)

EXAMPLE 69

(4-Fluoro-phenyl)-[1-(2-butoxy-3-phenoxy-propyl)-piperidin-4-yl]-methanone; hydrochloride The procedure given in Example 59 was followed using iodobutane as a reactant, instead of iodoethane, to give (4-fluoro-phenyl)-[1-(2-butoxy-3-phenoxy-propyl)-piperidin-4-yl]-methanone; hydrochloride.

1H-NMR (CDCl3, 200 MHz) δ12.0(br, 1H) 8.0(m, 2H), 7.2(m, 4H), 6.9(m, 3H), 4.4(m, 1H), 4.0(m, 3H), 3.8(m, 4H), 3.3(m, 5H), 2.7(m,2H), 2.1(m, 2H), 1.4(m, 3H). 0.9(m, 3H)

EXAMPLE 70

(4-Fluoro-phenyl)-[1-(2-benzyloxy-3-phenoxy-propyl)-piperidin-4-yl]-methanone; hydrochloride The procedure given in Example 59 was followed using benzyl bromide as a reactant, instead of iodoethane, to give (4-fluoro-phenyl)-[1-(2-benzyloxy-3-phenoxy-propyl)-piperidin-4-yl]-methanone; hydrochloride.

1H-NMR (CDCl3, 200 MHz) δ12.0(br, 1H) 8.0(m, 2H), 7.2(m, 8H), 6.9(m, 4H), 4.9(m, 3H), 4.5(m, 1H), 4.1(m, 3H), 3.3(m, 5H), 2.6(m, 2H), 2.2(m, 2H)

EXAMPLE 71

(4-Fluoro-phenyl)-{1-[2-(4-isopropyl-phenyl)-2-[1,2,4]triazoyl-1-yl-ethyl]-piperidin-4-yl}-methanone trihydrochloride A mixture of 4-(4-fluorobenzoyl)piperidine (5 mmol) and 2-(4-isopropylphenyl)oxirane (5 mmol) was refluxed in 30 ml of isopropanol for 4 h. This solution was then concentrated on a rotary evaporator and diluted with ethyl acetate. This mixture was then washed with brine, the resulting organic layer was dried and concentrated in vacuo. The crude product was dissolved in dichloromethane (50 ml) and was added with methanesulfonyl chloride (2 eq.) and triethylamine (3 eq.) at 0° C. The reaction mixture was stirred at room temperature for 1 h. This solution was then added triethylamine (3 eq.), followed by the addition of excess 1,2,4-triazole (>3 eq.). After 4 hours stirring at room temperature, this solution was concentrated on a rotary evaporator and diluted with ethyl acetate. The organic layer was washed 2 times with saturated sodium bicarbonate solution, dried and concentrated in vacuo. The residue was purified by column chromatography (ethyl acetate:hexane=1:1). The resulting (4-fluoro-phenyl)-{1-[2-(4-isopropyl-phenyl)-2-[1,2,4]triazoyl-1-yl-ethyl]-piperidin-4-yl}-methanone was dissolved in dichloromethane and the solution was treated with a solution of HCl in ethyl ether. The resulting precipitate was filtered to give (4-fluoro-phenyl)-{1-[2-(4-isopropyl-phenyl)-2-[1,2,4]triazoyl-1-yl-ethyl]-piperidin-4-yl}-methanone trihydrochloride.

1H-NMR(DMSO-D6, 200 MHz), δ1.14(d,6H), 1.93(m, 4H), 2.89(m,1H), 3.16(m,2H), 3.71(m,4H), 4.39(m,1H), 5.82(br,2H), 6.59(d,1H), 7.32(m,6H), 8.09(t,2H), 8.25(s, 1H), 9.08(s,1H), 11.17(br,1H)

EXAMPLE 72

(4-Fluoro-phenyl)-[1-(2-phenyl-2-[1,2,4]triazol-1-yl-ethyl)-piperidin-4-yl]-methanone The procedure given in Example 71 was followed using styrene oxide as a reactant, instead of 2-(4-isopropylphenyl)oxirane, to give (4-fluoro-phenyl)-[1-(2-phenyl-2-[1,2,4]triazoyl-1-yl-ethyl)-piperidin-4-yl]-methanone.

1H-NMR(CDCl$_3$, 200 MHz), δ1.72(m,4H), 2.28(m,2H), 2.79(d,1H), 2.95(d,1H), 3.01(d,1H), 3.16(m,1H), 3.41(q, 1H), 5.52(q,1H), 7.09(t,2H), 7.29(m,5H), 7.91(t,2H), 7.96 (s,1H), 8.25(s,1H)

EXAMPLE 73

{1-[2-(3,4-Dimethyl-phenyl)-2-[1,2,4]triazol-1-yl-ethyl]-piperidin-4-yl}-(4-fluoro-phenyl)-methanone The procedure given in Example 71 was followed using 3,4-dimethylstyrene oxide as a reactant, instead of 2-(4-isopropylphenyl)oxirane, to give {1-[2-(3,4-dimethyl-phenyl)-2-[1,2,4]triazoyl-1yl-ethyl]-piperidin-4-yl}-(4-fluoro-phenyl)-methanone 1H-NMR(CDCl$_3$, 200 MHz), δ1.76(m,4H), 2.25(s,6H), 2.33(m,2H), 2.80(d,1H), 2.97(m,2H), 3.17(m,1H), 3.39(q, 1H), 5.48(q,1H), 7.11(m,5H), 7.92(m,3H), 8.22(s,1H)

EXAMPLE 74

(4-Fluoro-phenyl)-[1-(4-phenyl-2-[1,2,4]triazoyl-1-yl-butyl)-piperidin-4-yl]-methanone The procedure given in Example 71 was followed using 2-phenethyl-oxirane as a reactant, instead of 2-(4- isopropylphenyl)oxirane, to give (4-fluoro-phenyl)-[1-(4-phenyl-2-[1,2,4]triazoyl-1-yl-butyl)-piperidin-4-yl]-methanone.

1H-NMR(CDCl₃, 200 MHz), δ1.74(m,4H), 2.18(m,2H), 2.32(m,2H), 2.54(m,2H), 2.71(t,1H), 2.87(m,1H), 3.12(m, 1H), 3.57(m,2H), 4.27(m,1H), 7.21(m,7H), 7.92(m,4H),

EXAMPLE 75

{1-[2-(4-tert-Butyl-phenyl)-2-[1,2,4]triazol-1-yl-ethyl]-piperidin-4-yl}-(4-fluoro-phenyl)-methanone The procedure given in Example 71 was followed using 4-tert-butylstyrene oxide as a reactant, instead of 2-(4-isopropylphenyl)oxirane, to give {1-[2-(4-tert-butyl-phenyl)-2-[1,2,4]triazol-1-yl-ethyl]-piperidin-4-yl}-(4-fluoro-phenyl)-methanone.

1H-NMR(CDCl₃, 200 MHz), δ1.27(s,9H), 2.73(m,4H), 2.25(m,2H), 2.77(d,1H), 2.97(m,2H), 3.14(m,1H), 3.39(q, 1H), 5.49(q,1H), 7.09(t,2H), 7.29(q,4H), 7.94(m,3H), 8.21 (s,1H)

EXAMPLE 76

{1-[2-(2-Chloro-phenyl)-2-[1,2,4]triazol-1-yl-ethyl]-piperidin-4-yl}-(4-fluoro-phenyl)-methanone The procedure given in Example 71 was followed using 2-chlorostyrene oxide as a reactant, instead of 2-(4-isopropylphenyl)oxirane, to give {1-[2-(2-chloro-phenyl)-2-[1,2,4]triazol-1-yl-ethyl)-piperidin-4-yl}-(4-fluoro-phenyl)-methanone.

1H-NMR(CDCl₃, 200 MHz), δ1.73(m,4H), 2.31(m,2H), 2.80(d,1H), 2.95(q,1H), 3.09(m,2H), 3.39(q,1H), 6.05(q, 1H), 7.09(t,2H), 7.26(m,2H), 7.37(m,2H), 7.89(q,2H), 7.95 (s,1H), 8.27(s,1H)

EXAMPLE 77

(4-Fluoro-phenyl)-{1-[2-(4-nitro-phenyl)-2-[1,2,4] triazol-1-yl-ethyl]-piperidin-4-yl}yl-methanone The procedure given in Example 71 was followed using 4-nitrostyrene oxide as a reactant, instead of 2-(4-isopropylphenyl)oxirane, to give (4-fluoro-phenyl)-{1-[2-(4-nitro-phenyl)-2-[1,2,4]triazol-1-yl-ethyl]-piperidin-4-yl}-methanone.

1H-NMR(CDCl₃, 200 MHz), δ1.74(m,4H), 2.31(q,2H), 2.81(d,1H), 2.93(m,1H), 3.11(m,2H), 3.36(q,1H), 5.59(m, 1H), 7.12(t,2H), 7.49(d,2H), 7.92(m,3H), 819(m,2H), 8.29 (s, 1H)

EXAMPLE 78

(4-Fluoro-phenyl)-[1-(2-naphthalen-2-yl-2-[1,2,4] triazol-1-yl-ethyl]-piperidin-4-yl]-methanone The procedure given in Example 71 was followed using 2-naphthalene oxide as a reactant, instead of 2-(4-isopropylphenyl)oxirane, to give (4-fluoro-phenyl)-[1-(2-naphthalen-2-yl-2-[1,2,4]triazol-1-yl-ethyl)-piperidin-4-yl]-methanone.

1H-NMR(CDCl₃, 200 MHz), δ1.79(m,4H), 2.33(m,2H), 2.85(d,1H), 3.10(m,3H), 3.57(m,1H), 5.73(m,1H), 7.12(t, 2H), 7.49(m,3H), 7.85(m,7H), 8.29(s, 1H)

EXAMPLE 79

(4-Fluoro-phenyl)-{1-[2-[1,2,4]triazol-1-yl-2-(4-trifluoromethyl-phenyl)-ethyl]-piperidin-4-yl}-methanone The procedure given in Example 71 was followed using 4-trifluoromethylstyrene oxide as a reactant, instead of 2-(4-isopropylphenyl)oxirane, to give (4-fluoro-phenyl)-{1-[2-[1,2,4]triazol-1-yl-2-(4-trifluoromethyl-phenyl)-ethyl]-piperidin-4-yl}-methanone.

1H-NMR(CDCl₃, 200 MHz), δ1.76(m,4H), 2.37(m,2H), 2.81(d,1H), 3.01(m,2H), 3.19(m,1H), 3.39(m,1H), 5.59(m, 1H), 7.13(,2H), 7.43(d,2H), 7.63(d,2H), 7.91(m,3H), 8.29 (s,1H)

EXAMPLE 80

(4-Fluoro-phenyl)-[1-(2-phenyl-2-tetrazol-1-yl-ethyl)-piperidin-4-yl]-methanone

The procedure given in Example 71 was followed using styrene oxide and tetrazole as reactants, instead of 2-(4-isopropylphenyl)oxirane and 1,2,4-triazole, to give (4-fluoro-phenyl)-[1-(2-phenyl-2-tetrazol-1-yl-ethyl)-piperidin-4-yl]-methanone.

1H-NMR(CDCl₃, 200 MHz), δ1.75(m,4H), 2.31(m,2H), 2.79(d,1H), 3.03(m,2H), 3.18(m,1H), 3.42(q,1H), 5.79(q, 1H), 7.07(t,2H), 7.38(m,5H), 7.92(t,2H), 8.79(s, 1H)

EXAMPLE 81

(4-Fluoro-phenyl)-[1-(2-phenyl-2-[1,2,3]triazol-1-yl-ethyl)-piperidin-4-yl]-methanone The procedure given in Example 71 was followed using styrene oxide and 1,2,3-triazole as reactants, instead of 2-(4-isopropylphenyl)oxirane and 1,2,4-triazole, to give (4-fluoro-phenyl)-[1-(2-phenyl-2-[1,2,3]triazol-1-yl-ethyl)-piperidin-4-yl]-methanone.

1H-NMR(CDCl₃, 200 MHz), δ1.69(m,4H), 2.27(m,2H), 2.91(q,2H), 3.13(m,2H), 3.47(m,1H), 5.79(q, 1H), 7.07(t, 2H), 7.25(m,5H), 7.63(d,2H), 7.91(t,2H)

EXAMPLE 82

(4-Fluoro-phenyl)-[1-(2-imidazol-1-yl-2-phenyl-ethyl)-piperidin-4-yl]-methanone

The procedure given in Example 71 was followed using styrene oxide and imidazole as reactants, instead of 2-(4-isopropylphenyl)oxirane and 1,2,4-triazole, to give (4-fluoro-phenyl)-[1-(2-imidazol-1-yl-2-phenyl-ethyl)-piperidin-4-yl]-methanone.

1H-NMR(CDCl₃, 200 MHz), δ1.79(m,4H), 2.22(m,2H), 2.79(d,1H), 2.99(m,2H), 3.11(m,2H), 5.29(m,1H), 7.05(m, 6H), 7.29(m,3H), 7.63(s,1H), 7.93(m,2H)

EXAMPLE 83

Carbonic acid 1-(4-ethyl-phenyl)-2-[4-(4-fluoro-benzoyl)-piperidin-1-yl]-ethyl ester methyl ester A mixture of 4-(4-fluorobenzoyl)piperidine (5 mmol) and 2-(4-ethylphenyl)-oxirane (5 mmol) was refluxed in 30 ml of isopropanol for 4 h. This solution was then concentrated on a rotary evaporator and diluted with ethyl acetate. This mixture was then washed with brine, the resulting organic layer was dried and concentrated in vacuo. The crude product was dissolved in THF (50 ml) and was added with 1,1'-carbonyl diimidazole (2 mmol) at 0° C. The reaction mixture was stirred at room temperature for 4 h, followed by the addition of excess methanol (10 ml) at 0° C. After 5 h stirring at room temperature, water was added to terminate the reaction. The organic layer was extracted 3 times with dichloromethane, dried and concentrated in vacuo. The resulting carbonic acid 1-(4-ethyl-phenyl)-2-[4-(4-fluorobenzoyl)-piperidin-1-yl]-ethyl ester methyl ester was obtained by column chromatography.

1H-NMR (CDCl3, 200 MHz) δ7.9(m, 2H), 7.2(m, 6H), 5.8(m, 1H), 3.8(s, 3H), 3.0(m, 4H), 2.6(m, 3H), 2.2(m, 2H), 1.8(m, 4H), 1.2(m, 3H)

EXAMPLE 84

Carbonic acid 2-[4-(4-fluoro-benzoyl)-piperidin-1-yl]-1-phenyl-ethyl ester methyl ester The procedure given in Example 83 was followed using styrene oxide as a reactant, instead of 2-(4-ethylphenyl)-oxirane, to give carbonic acid 2-[4-(4-fluoro-benzoyl)-piperidin-1-yl]-1-phenyl-ethyl ester methyl ester.

1H-NMR (CDCl3, 200 MHz) δ8.0(m, 2H), 7.3(m, 5H), 7.1(m, 2H), 5.9(m, 1H), 3.8(s, 3H), 3.0(m, 4H), 2.6(dd 1H), 2.3(m, 2H), 1.8(m, 4H)

EXAMPLE 85

Carbonic acid ethyl ester 2-[4-(4-fluoro-benzoyl)-piperidin-1-yl]-1-phenyl-ethyl ester The procedure given in Example 83 was followed using styrene oxide and ethanol as reactants, instead of 2-(4-ethylphenyl)-oxirane and methanol, to give carbonic acid ethyl ester 2-[4-(4-fluoro-benzoyl)-piperidin-1-yl]-1-phenyl-ethyl ester.

1H-NMR (CDCl3, 200 MHz) δ8.0(m, 2H), 7.3(m, 5H), 7.1(m, 2H), 5.9(m, 1H), 4.2(m, 2H), 3.0(m, 4H), 2.6(dd 1H), 2.3(m, 2H), 1.8(m, 4H), 1.3(m, 3H)

EXAMPLE 86

Carbonic acid 2-[4-(4-fluoro-benzoyl)-piperidin-1-yl]-1-phenyl-ethyl ester propyl ester The procedure given in Example 83 was followed using styrene oxide and propanol as reactants, instead of 2-(4-ethylphenyl)-oxirane and methanol, to give carbonic acid 2-[4-(4-fluoro-benzoyl)-piperidin-1-yl]-1-phenyl-ethyl ester propyl ester.

1H-NMR (CDCl3, 200 MHz) δ7.9(m, 2H), 7.3(m, 5H), 7.1(m, 2H), 5.8(m, 1H), 4.1(m, 2H), 3.0(m, 4H), 2.6(dd, 1H), 2.2(m, 2H), 1.8(m, 6H), 1.0(m, 3H)

EXAMPLE 87

Carbonic acid 2-[4-(4-fluoro-benzoyl)-piperidin-1-yl]-1-phenyl-ethyl ester isopropyl ester The procedure given in Example 83 was followed using styrene oxide and isopropanol as reactants, instead of 2-(4-ethylphenyl)-oxirane and methanol, to give carbonic acid 2-[4-(4-fluoro-benzoyl)-piperidin-1-yl]-1-phenyl-ethyl ester isopropyl ester.

1H-NMR (CDCl3, 200 MHz) δ8.0(m, 2H), 7.3(m, 5H), 7.1(m, 2H), 5.8(m, 1H), 4.8(m, 1H), 3.0(m, 4H), 2.6(m, 1H), 2.2(m, 2H), 1.8(m, 4H), 1.3(m, 6H)

EXAMPLE 88

Carbonic acid 2-[4-(4-fluoro-benzoyl)-piperidin-1-yl]-1-phenyl-ethyl ester phenyl ester The procedure given in Example 83 was followed using styrene oxide and phenol as a reactant, instead of 2-(4-ethylphenyl)-oxirane and methanol, to give carbonic acid 2-[4-(4-fluoro-benzoyl)-piperidin-1-yl]-1-phenyl-ethyl ester phenyl ester.

1H-NMR (CDCl3, 200 MHz) δ8.0(m, 2H), 7.4(m, 7H), 7.2(m, 5H), 5.9(m, 1H), 3.1(m, 4H), 2.7(dd, 1H), 2.3(m, 2H), 1.8(m, 4H)

EXAMPLE 89

Carbonic acid benzyl ester 2-[4-(4-fluoro-benzoyl)-piperidin-1-yl]-1-phenyl-ethyl ester The procedure given in Example 83 was followed using styrene oxide and benzyl alcohol as reactants, instead of 2-(4-ethylphenyl)-oxirane and methanol, to give carbonic acid benzyl ester 2-[4-(4-fluoro-benzoyl)-piperidin-1-yl]-1-phenyl-ethyl ester.

1H-NMR (CDCl3, 200 MHz) δ8.0(m, 2H), 7.4(m, 10H), 7.1(m, 2H), 5.8(m, 1H), 5.2(m, 2H), 3,0(m, 4H), 2.6(dd, 1H), 2.2(m, 2H), 1.8(m, 4H)

EXAMPLE 90

Carbonic acid 1-[4-(4-fluoro-benzoyl)-piperidin-1-ylmethyl]-3-phenyl-propyl ester methyl ester The procedure given in Example 83 was followed using 2-phenethyl-oxirane as a reactant, instead of 2-(4-ethylphenyl)-oxirane, to give carbonic acid 1-[4-(4-fluoro-benzoyl)-piperidin-1-ylmethyl]-3-phenyl-propyl ester methyl ester.

1H-NMR (CDCl3, 200 MHz) δ8.0(m, 2H), 7.2(m, 7H), 4.9(m, 1H), 3.8(s, 3H), 3.0(m, 3H), 2.6(m, 4H), 2.2(m, 2H), 2.0(m, 2H), 1.8(m, 4H)

EXAMPLE 91

Carbonic acid 1-(3-chloro-phenyl)-2-[4-(4-fluoro-benzoyl)-piperidin-1-yl]-ethyl ester isopropyl ester The procedure given in Example 83 was followed using 3-chlorostyrene oxide and isopropanol as reactants, instead of 2-(4-ethylphenyl)-oxirane and methanol, to give carbonic acid 1-(3-chloro-phenyl)-2-[4-(4-fluoro-benzoyl)-piperidin-1-yl]-ethyl ester isopropyl ester.

1H-NMR (CDCl3, 200 MHz) δ8.0(m, 2H), 7.3(m, 4H), 7.1(m, 2H), 5.8(m, 1H), 4.9(m, 1H), 3.0(m, 4H), 2.6(dd, 1H), 2.2(m, 2H), 1.8(m, 4H), 1.3(m, 6H)

EXAMPLE 92

Carbonic acid 1-(4-chloro-phenyl)-2-[4-(4-fluoro-benzoyl)-piperidin-1-yl]-ethyl ester isopropyl ester The procedure given in Example 83 was followed using 4-chlorostyrene oxide and isopropanol as reactants, instead of 2-(4-ethylphenyl)-oxirane and methanol, to give carbonic acid 1-(4-chloro-phenyl)-2-[4-(4-fluoro-benzoyl)-piperidin-1-yl]-ethyl ester isopropyl ester.

1H-NMR (CDCl3, 200 MHz) δ8.0(m, 2H), 7.3(m, 5H), 7.1(m, 2H), 5.8(m, 1H), 4.9(m, 1H), 3.0(m, 4H), 2.6(dd, 1H), 2.2(m, 2H), 1.8(m, 4H), 1.3(m, 6H)

EXAMPLE 93

Carbonic acid 1-(4-cyano-phenyl)-2-[4-(4-fluoro-benzoyl)-piperidin-1-yl]-ethyl ester isopropyl ester The procedure given in Example 83 was followed using 4-oxiranyl-benzonitrile and isopropanol as reactants, instead of 2-(4-ethylphenyl)-oxirane and methanol, to give carbonic acid 1-(4-cyano-phenyl)-2-[4-(4-fluoro-benzoyl)-piperidin-1-yl]-ethyl ester isopropyl ester.

1H-NMR (CDCl3, 200 MHz) δ8.0(m, 2H), 7.7(d, 2H), 7.5(d, 2H), 7.1(m, 2H), 5.8(m, 1H), 4.9(m, 1H), 3.0(m, 4H), 2.6(dd 1H), 2.2(m, 2H), 1.8(m, 4H), 1.3(m, 6H)

EXAMPLE 94

Carbonic acid 2-[4-(3-chloro-benzoyl)-piperidin-1-yl]-1-phenoxymethyl-ethyl ester isopropyl ester The procedure given in Example 83 was followed using styrene oxide and isopropanol as reactants, instead of 2-(4-ethylphenyl)-oxirane and methanol, to give carbonic acid 2-[4-(3-chloro-benzoyl)-piperidin-1-yl]-1-phenoxymethyl-ethyl ester isopropyl ester.

1H-NMR (CDCl3, 200 MHz) δ7.8(m, 2H), 7.3(m, 4H), 6.9(m, 3H), 5.1(m, 1H), 4.9(m, 1H), 4.1(m, 2H), 3.1(m, 1H), 3.0(m, 2H), 2.7(m, 2H), 2.2(m, 2H), 1.8(m, 4H), 6H)

What is claimed is:

1. A racemic or enantiomerically enriched benzoyl piperidine compound represented by the following structural formula (I):

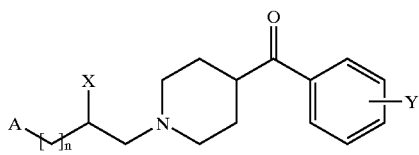

(I)

wherein
n is o; and
A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl and phenyl; thienyl; naphthyl; pyridyl; and quinolyl; or
n is an integer from 1 to 2; and
A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl and phenyl; thienyl; naphthyl; pyridyl; and quinolyl;
X is selected from the group consisting of O-carbamoyl, straight or branched chain alkoxy of from 1 to 4 carbon atoms, imidazole, triazole, tetrazole and carbonate; and
Y is selected from the group consisting of hydrogen, halogen, straight or branched chain alkyl of from 1 to 4 carbon atoms and straight or branched chain alkoxy of from 1 to 3 carbon atoms;
and pharmaceutically acceptable salts thereof.

2. A racemic or enantiomerically enriched O-carbamoyl benzoyl piperidine compound represented by the structural formula (V):

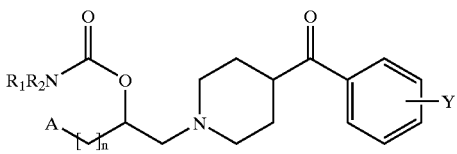

(V)

wherein
n is o; and
A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl; or
n is an integer from 1 to 2; and
A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl;
Y is selected from the group consisting of hydrogen, halogen, straight or branched chain alkyl of from 1 to 4 carbon atoms and straight or branched chain alkoxy of from 1 to 3 carbon atoms; and
R1 and R2 may be the same with or different from each other and are independently selected from the group consisting of hydrogen, methoxy, benzyl and 5 to 7-membered aliphatic cyclic compounds;
and pharmaceutically acceptable salts thereof.

3. A racemic or enantiomerically enriched alkoxy benzoyl piperidine compound represented by the structural formula (VIII):

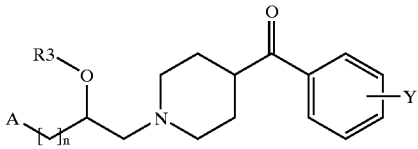

(VIII)

wherein
n is o; and
A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyl; thienyl; naphthyl; pyridyl; and quinolyl; or
n is an integer from 1 to 2; and
A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano, trifluoromethyl, trifluoromethoxy, methanesulfonyl, phenyl; thienyl; naphthyl; pyridyl; and quinolyl;

49

Y is selected from the group consisting of hydrogen, halogen, straight or branched chain alkyl of from 1 to 4 carbon atoms, and straight or branched chain alkoxy of from 1 to 3 carbon atoms; and R3 is selected from the group consisting of straight or branched chain alkyl of from 1 to 4 carbon atoms, aliphatic cyclic compound of from 5 to 7 carbon atoms, and benzyl;

and pharmaceutically acceptable salts thereof.

4. A racemic or enantiomerically enriched azole benzoyl piperidine compound represented by the structural formula (XIV):

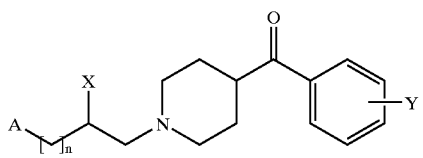

(XIV)

wherein
n is an integer from 0 to 2;
A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro and trifluoromethyl; and naphthyl;
Y is selected from the group consisting of hydrogen, halogen, straight or branched chain alkyl of from 1 to 4 carbon atoms, and straight or branched chain alkoxy of from 1 to 3 carbon atoms; and
X is imidazole, triazole, or tetrazole moiety having the following formula (XII)

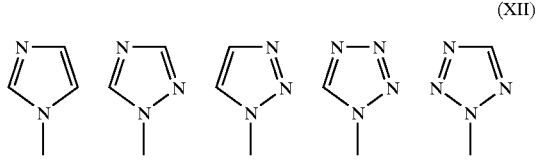

(XII)

and pharmaceutically acceptable salts thereof.

5. A racemic or enantiomerically enriched carbonate benzoyl piperidine compound represented by the structural formula (XVI):

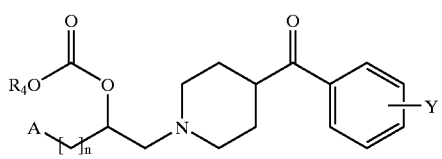

(XVI)

wherein
n is o; and
A is selected from the group consisting of phenyl which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano and trifluoromethyl; or

50 n is an integer from 1 to 2; and
A is selected from the group consisting of phenyl or phenoxy which may be substituted with one or more identical or different substituents selected from the group consisting of hydrogen, halogen, straight or branched chain alkyl of from 1 to 4 carbon atoms, straight or branched chain alkoxy of from 1 to 3 carbon atoms, nitro, cyano and trifluoromethyl;
Y is selected from the group consisting of hydrogen, halogen, straight or branched chain alkyl of from 1 to 4 carbon atoms, and straight or branched chain alkoxy of from 1 to 3 carbon atoms; and
R4 is selected from the group consisting of straight or branched chain alkyl of from 1 to 3 carbon atoms, phenyl and benzyl;

and pharmaceutically acceptable salts thereof.

6. A compound in accordance with claim 2 wherein said compound is carbamic acid 2-[4-(4-fluoro-benzoyl)-piperidin-1-yl]-1-phenyl-ethyl ester.

7. A compound in accordance with claim 2 wherein said compound is (S)-carbamic acid 2-[4-(4-fluoro-benzoyl)-piperidin-1-yl]-1-phenyl-ethyl ester.

8. A compound in accordance with claim 2 wherein said compound is (R)-carbamic acid 2-[4- 4-fluoro-benzoyl)-piperidin-1-yl]-1-phenyl-ethyl ester.

9. A compound in accordance with claim 2 wherein said compound is carbamic acid 1-(3-chloro-phenyl)-2-[4-(4-fluoro-benzoyl)-piperidin-1-yl]-ethyl ester.

10. A compound in accordance with claim 2 wherein said compound is carbamic acid 1-(3,4-dichloro-phenyl)-2-[4-(4-fluoro-benzoyl)-piperidin-1-yl]-ethyl ester.

11. A compound in accordance with claim 2 wherein said compound is benzyl-carbamic acid 2-[4-(4-fluoro-benzoyl)-piperidin-1-yl]-1-phenyl-ethyl ester.

12. A compound in accordance with claim 2 wherein said compound is carbamic acid 2-[4-(4-fluoro-benzoyl)-piperidin-1-yl]-1-(3-nitro-phenyl)-ethyl ester.

13. A compound in accordance with claim 2 wherein said compound is carbamic acid 2-[4-(4-fluoro-benzoyl)-piperidin-1-yl]-1-(4-trifluoromethyl-phenyl)-ethyl ester.

14. A compound in accordance with claim 2 wherein said compound is carbamic acid 1-[4-(4-fluoro-benzoyl)-piperidin-1-ylmethyl]-2-phenoxy-ethyl ester.

15. A compound in accordance with claim 2 wherein said compound is carbamic acid azepane-1-carboxylic acid 1-[4-(4-fluoro-benzoyl)-piperidin-1-ylmethyl]-2-phenoxy-ethyl ester.

16. A compound in accordance with claim 3 wherein said compound is (4-fluoro-phenyl)-{1-[2-methoxy-2-(4-nitro-phenyl)-ethyl]-piperidin-4-yl}-methanone.

17. A compound in accordance with claim 3 wherein said compound is (S)-(4-fluoro-phenyl)-{1-[2-methoxy-2-(4-nitro-phenyl)-ethyl]-piperidin-4-yl}-methanone.

18. A compound in accordance with claim 3 wherein said compound is (R)-(4-fluoro-phenyl)-{1-[2-methoxy-2-(4-nitro-phenyl)-ethyl]-piperidin-4-yl}-methanone.

19. A compound in accordance with claim 3 wherein said compound is (4-fluoro-phenyl)-{1-[2-(4-isopropyl-phenyl)-2-methoxy-ethyl]-piperidin-4-yl}-methanone.

20. A compound in accordance with claim 3 wherein said compound is (S)-(4-fluoro-phenyl)-{1-[2-(4-isopropyl-phenyl)-2-methoxy-ethyl]-piperidin-4-yl}-methanone.

21. A compound in accordance with claim 3 wherein said compound is {1-[2-(4-ethyl-phenyl)-2-methoxy-ethyl]-piperidin-4-yl}-(4-fluoro-phenyl)-methanone.

22. A compound in accordance with claim 3 wherein said compound is (S)-{1-[2-(4-ethyl-phenyl)-2-methoxy-ethyl]-piperidin-4-yl)-(4-fluoro-phenyl)-methanone.

23. A compound in accordance with claim 3 wherein said compound is {1-[2-ethoxy-2-(4-vitro-phenyl)-ethyl]-piperidin-4-yl}-(4-fluoro-phenyl)-methanone.

24. A compound in accordance with claim 3 wherein said compound is (4-fluoro-phenyl)-[1-(2-methoxy-3-phenoxy-propyl)-piperidin-4-yl]-methanone.

25. A compound in accordance with claim 3 wherein said compound is {1-[3-(4-Chloro-phenoxy)-2-methoxy-propyl]-piperidin-4-]}-(4-fluoro-phenyl)-methanone.

26. A compound in accordance with claim 4 wherein said compound is (4-fluoro-phenyl)-{1-[2-(4-isopropyl-phenyl)-2-[1,2,4]triazol-1-yl-ethyl]-piperidin-4-yl}-methanone.

27. A compound in accordance with claim 4 wherein said compound is {1-[2-(3,4-dimethyl-phenyl)-2-[1,2,4]triazol-1-yl-ethyl]-piperidin-4-yl}-(4-fluoro-phenyl)-methanone.

28. A compound in accordance with claim 5 wherein said compound is carbonic acid 1-(4-ethyl-phenyl)-2-[4-(4-fluoro-benzoyl)-piperidin-1-yl]-ethyl ester methyl ester.

29. A compound in accordance with claim 5 wherein said compound is carbonic acid 1-(3-chloro-phenyl)-2-[4-(4-fluoro-benzoyl)-piperidin-1-yl]-isopropyl ester isopropyl ester.

30. A pharmaceutical composition which comprises a therapeutically effective amount of racemic or enantiomerically enriched compound of formula (I) in accordance with claim 1 for treating psychosis and cognition disorder.

31. A pharmaceutical composition which comprises a therapeutically effective amount of racemic or enantiomerically enriched compound of formula (V) in accordance with claim 2 for treating psychosis and cognition disorder.

32. A pharmaceutical composition which comprises a therapeutically effective amount of to racemic or enantiomerically enriched compound of formula (VIII) in accordance with claim 3 for treating psychosis and cognition disorder.

33. A pharmaceutical composition which comprises a therapeutically effective amount of racemic or enantiomerically enriched compound of formula (XIV) in accordance with claim 4 for treating psychosis and cognition disorder.

34. A pharmaceutical composition which comprises a therapeutically effective amount of racemic or enantiomerically enriched compound of formula (XVI) in accordance with claim 5 for treating psychosis and cognition disorder.

35. A method of treating psychosis in a mammal which comprises administering an effective amount of racemic or enantiomerically enriched compound of formula (I) according to claim 1 to a mammal in need of psychosis therapy.

36. A method of treating psychosis in a mammal which comprises administering an effective amount of racemic or enantiomerically enriched compound of formula (V) according to claim 2 to a mammal in need of psychosis therapy.

37. A method of treating psychosis in a mammal which comprises administering an effective amount of racemic or enantiomerically enriched compound of formula (VIII) according to claim 3 to a mammal in need of psychosis therapy.

38. A method of treating psychosis in a mammal which comprises administering an effective amount of racemic or enantiomerically enriched compound of formula (XIV) according to claim 4 to a mammal in need of psychosis therapy.

39. A method of treating psychosis in a mammal which comprises administering an effective amount of racemic or enantiomerically enriched compound of formula (XVI) according to claim 5 to a mammal in need of psychosis therapy.

\* \* \* \* \*

(12) EX PARTE REEXAMINATION CERTIFICATE (7690th)
United States Patent
Choi et al.

(10) Number: US 6,770,659 C1
(45) Certificate Issued: Aug. 17, 2010

(54) BENZOYL PIPERIDINE COMPOUNDS

(75) Inventors: Yong-Moon Choi, Towaco, NJ (US); Yong-Kil Kim, Daejeon (KR); Jin-Uk Yoo, Daejeon (KR); Eun-Ah Paek, Daejeon (KR); Chun-Eung Park, Daejeon (KR); Sung-Yong Seo, Daejeon (KR); Coo-Min Chung, Daejeon (KR); Joon Heo, Daejeon (KR)

(73) Assignee: SK Holdings Co, Ltd., Jongro-Gu, Seoul (KR)

Reexamination Request:
No. 90/010,807, Dec. 30, 2009

Reexamination Certificate for:
Patent No.: 6,770,659
Issued: Aug. 3, 2004
Appl. No.: 10/228,869
Filed: Aug. 26, 2002

(51) Int. Cl.
*C07D 211/32* (2006.01)
*C07D 211/00* (2006.01)

(52) U.S. Cl. .............. 514/326; 514/212; 514/235.5; 514/316; 514/330; 540/597; 544/130; 546/189; 546/210; 546/211; 546/225

(58) Field of Classification Search .............. None
See application file for complete search history.

(56) References Cited

U.S. PATENT DOCUMENTS

| 3,576,810 A | 4/1971 | Duncan, Jr. et al. |
| 4,559,349 A | 12/1985 | Storni |
| 4,711,899 A | 12/1987 | Gaudilliere et al. |
| 4,948,799 A | 8/1990 | Antoku et al. |

FOREIGN PATENT DOCUMENTS

| CA | 2186010 | 9/1995 |
| EP | 0124476 A1 | 11/1984 |
| EP | 0202164 | 11/1986 |
| EP | 0222702 A2 | 5/1987 |
| EP | 0261688 A1 | 3/1988 |
| EP | 0288 563 | 11/1988 |
| EP | 0 409 236 A1 | 1/1991 |

OTHER PUBLICATIONS

Supplementary European Search Report.

*Primary Examiner*—Evelyn Huang

(57) ABSTRACT

Provided herein are racemic or enantiomerically enriched benzoyl piperidine compounds and pharmaceutically useful salts thereof, pharmaceutical compositions comprising an effective amount of racemic or enantiomerically enriched benzoyl piperidine compounds to treat central nervous system diseases and methods of treating central nervous system diseases in a mammal, in particular psychoses and cognition disorders.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 3, 16-25, 30, 32, 35 and 37 are cancelled.
Claims 2, 4-15, 26-29, 31, 33-34, 36 and 38-39 were not reexamined.

\* \* \* \* \*